United States Patent
Parker et al.

(10) Patent No.: US 9,719,982 B2
(45) Date of Patent: *Aug. 1, 2017

(54) DEVICES COMPRISING MUSCLE THIN FILMS AND USES THEREOF IN HIGH THROUGHPUT ASSAYS FOR DETERMINING CONTRACTILE FUNCTION

(71) Applicant: President and Fellows of Harvard College, Cambridge, MA (US)

(72) Inventors: Kevin Kit Parker, Cambridge, MA (US); Adam W. Feinberg, Pittsburgh, PA (US); Patrick W. Alford, Minneapolis, MN (US); Anna Grosberg, Irvine, CA (US); Mark Daniel Brigham, Cambridge, MA (US); Josue A. Goss, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/642,906

(22) Filed: Mar. 10, 2015

(65) Prior Publication Data

US 2016/0003806 A1 Jan. 7, 2016

Related U.S. Application Data

(63) Continuation of application No. 13/318,227, filed as application No. PCT/US2010/033220 on Apr. 30, 2010, now Pat. No. 9,012,172.

(Continued)

(51) Int. Cl.
*G01N 33/50* (2006.01)
*C12Q 1/02* (2006.01)
*C40B 30/06* (2006.01)

(52) U.S. Cl.
CPC ..... *G01N 33/5061* (2013.01); *G01N 33/5032* (2013.01); *G01N 33/5088* (2013.01);
(Continued)

(58) Field of Classification Search
None
See application file for complete search history.

(56) References Cited

U.S. PATENT DOCUMENTS 9,012,172 B2 4/2015 Parker et al.
2004/0009566 A1 1/2004 Okano et al.
(Continued)

FOREIGN PATENT DOCUMENTS

WO WO-2008/051265 A2 5/2008
WO WO 2008051265 A2 * 5/2008 ........... C12N 5/0062
(Continued)

OTHER PUBLICATIONS

Alford et al., "Biohybrid thin films for measuring contractility in engineered cardiovascular muscle" *Biomaterials* 31, 2010, pp. 3613-3621.
(Continued)

*Primary Examiner* — Kaijiang Zhang
(74) *Attorney, Agent, or Firm* — McCarter & English, LLP; Maria Laccotripe Zacharakis; Deborah L. Nagle

(57) ABSTRACT

The present invention provides high throughput assays for identifying compounds that modulate a contractile function, as well as devices suitable for use in these assays.

23 Claims, 21 Drawing Sheets

Related U.S. Application Data

(60) Provisional application No. 61/174,511, filed on May 1, 2009.

(52) U.S. Cl.
CPC .............. *C12Q 1/025* (2013.01); *C40B 30/06* (2013.01); *G01N 2500/10* (2013.01)

(56) References Cited

U.S. PATENT DOCUMENTS

| | | |
|---|---|---|
| 2004/0078090 A1 | 4/2004 | Binette et al. |
| 2004/0101819 A1 | 5/2004 | Montemagno et al. |
| 2005/0080402 A1 | 4/2005 | Santamore et al. |
| 2005/0085847 A1 | 4/2005 | Galdonik et al. |
| 2006/0003439 A1 | 1/2006 | Ismagilov et al. |
| 2007/0178534 A1* | 8/2007 | Murphy et al. ........ B82Y 15/00 435/7.2 |
| 2009/0317852 A1 | 12/2009 | Parker et al. |
| 2010/0196432 A1 | 8/2010 | Feinberg et al. |
| 2010/0330644 A1 | 12/2010 | Feinberg et al. |
| 2011/0189719 A1 | 8/2011 | Kuo et al. |
| 2012/0142556 A1 | 6/2012 | Parker et al. |

FOREIGN PATENT DOCUMENTS

| | | |
|---|---|---|
| WO | WO-2011/102991 A1 | 8/2011 |
| WO | WO-2012/006320 A1 | 1/2012 |
| WO | WO-2012/048242 A1 | 4/2012 |

OTHER PUBLICATIONS

Bray et al., "Sarcomere Alignment is Regulated by Myocyte Shape" *Cell Motility and the Cytoskeleton*, 2008, 65(8), pp. 641-651.

Bursac et al., "Cardiomyocyte cultures with controlled macroscopic anisotropy." *Circulation Rearch*, 2002, vol. 91, pp. e45-e54.

Grosberg et al., "Ensembles of engineered cardiac tissues for physiological and pharmacological study: Heart on a chip." *Lab Chip*, 2011, vol. 11, p. 4165.

Lehnert et al., "Cell behavior on micropatterned substrata: limits of extracellular matrix geometry fro spreading and adhesion." *Journal of Cell Science*, 2004, vol. 117, pp. 41-52.

Parker et al., "Ectracellular matrix, mechanotransduction and struction hierarchies in heart tissue engineering." *Phil Trans R. Soc B*, Epub Jun. 22, 2007, vol. 362, pp. 1267-1279.

Yang et al., "Fabrication of well-defined PLGA scaffolds using novel microembossing and carbon dioxide bonding", Biomaterials, 2005, vol. 26, pp. 2585-2594.

Xi et al., "Development of a Self-Assembled Muscle-Powered Piezoelectric Microgenerator", NSTI-Nanotech, 2004, vol. 1, pp. 3-6.

Spring, "Electronic Imaging in Neuroscience," Curr. Protoc. Neurosci. 2002,2.4.1-2.4.9.

Park et al., "Real-Time Measurement of the Contractile Forces of Self-Organized Cardiomyocytes on Hybrid Biopolymer Microcantilevers," Anal. Chem. 2005, 77:6571-6580.

Mao et al., "Capillary isoelectric focusing with whole column imaging detection for analysis of proteins and peptides," J. Biochem. Biophys. Methods 1999, 39:93-110.

* cited by examiner

FIG. 9A
SCHEMATIC OF PLATE FABRICATION PROCESS
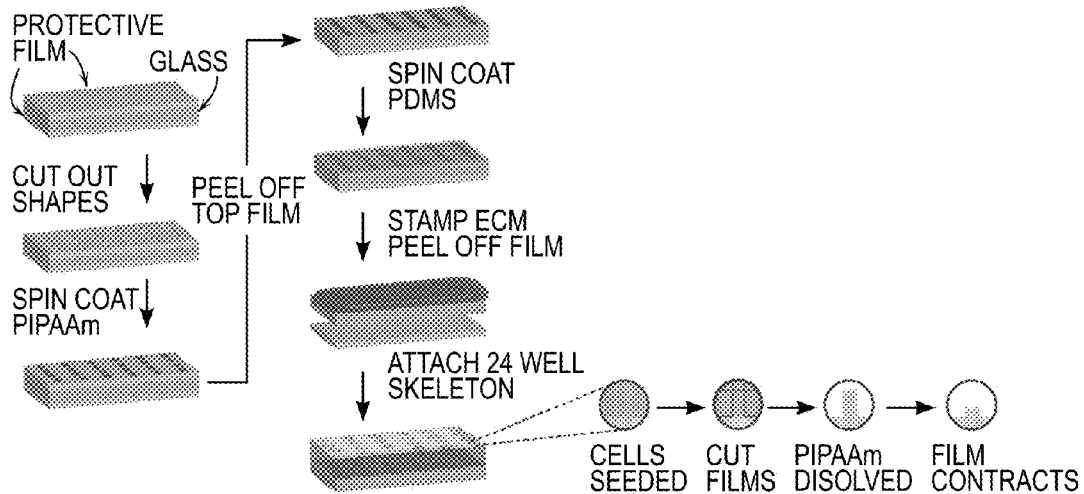
FIG. 9B
COMPLETED 24-WELL hMTF PLATE
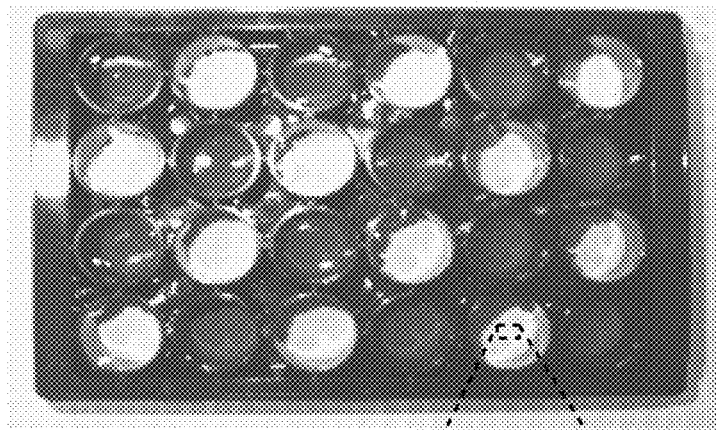
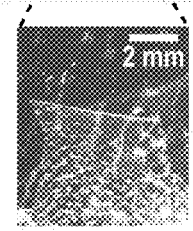
FIG. 9C

DEVICES COMPRISING MUSCLE THIN FILMS AND USES THEREOF IN HIGH THROUGHPUT ASSAYS FOR DETERMINING CONTRACTILE FUNCTION

RELATED APPLICATION

This application is a continuation of U.S. patent application Ser. No. 13/318,227, filed Oct. 31, 2011, which is a 35 U.S.C. §371 National Stage filing of International Application No. PCT/US2010/033220, filed on Apr. 30, 2010, which claims the benefit of and priority to U.S. Provisional Patent Application Ser. No. 61/174,511, filed on May 1, 2009. The entire contents of each of the foregoing incorporated herein by reference.

GOVERNMENT SUPPORT

The invention was supported, in whole or in part, by grant number N66001-08-C-2036 from the Defense Advanced Research Projects Agency under the United States Department of Defense. The United States Government has certain rights in the invention.

BACKGROUND OF THE INVENTION

Identification and evaluation of new therapeutic agents or identification of suspect disease associated targets typically employ animal models which are expensive, time consuming, require skilled animal-trained staff and utilize large numbers of animals. In vitro alternatives have relied on the use of conventional cell culture systems which are limited in that they do not allow the three-dimensional interactions that occur between cells and their surrounding tissue. This is a serious disadvantage as such interactions are well documented as having a significant influence on the growth and activity of cells in vivo since in vivo cells divide and interconnect in the formation of complex biological systems creating structure-function hierarchies that range from the nanometer to meter scales.

Efforts to build biosynthetic materials or engineered tissues that recapitulate these structure-function relationships often fail because of the inability to replicate the in vivo conditions that coax this behavior from ensembles of cells. For example, engineering a functional muscle tissue requires that the sarcomere and myofibrillogenesis be controlled at the micron length scale, while cellular alignment and formation of the continuous tissue require organizational cues over the millimeter to centimeter length scale. Thus, to build a functional biosynthetic material, the biotic-abiotic interface must contain the chemical and mechanical properties that support multiscale coupling.

Accordingly, there is a need for improved methods and systems that may be used for determining the effect of a test compound on biological relevant parameters in order to enhance and speed-up the drug discovery and development process.

SUMMARY OF THE INVENTION

Described herein are methods and devices for multiplex and high throughput, high content measurements of physiologically relevant properties of in vitro tissue constructs. The devices of the present invention can be used in, for example, high throughput screening assays to determine the effects of a test compound on living tissue by examining the effect of the test compound on various biological responses, such as for example, cell viability, cell growth, migration, differentiation and maintenance of cell phenotype, electrophysiology, metabolic activity, muscle cell contraction, osmotic swelling, structural remodeling and tissue level pre-stress.

Accordingly, in one aspect, the present invention provides methods for identifying a compound that modulates a contractile function. The methods include providing a plurality of muscle thin films; contacting a plurality of the muscle thin films with a test compound; and determining the effect of the test compound on a contractile function in the presence and absence of the test compound, wherein a modulation of the contractile function in the presence of the test compound as compared to the contractile function in the absence of the test compound indicates that the test compound modulates a contractile function, thereby identifying a compound that modulates a contractile function.

In another aspect, the present invention provides methods for identifying a compound useful for treating or preventing a muscle disease. The methods include providing a plurality of muscle thin films; contacting a plurality of the muscle thin films with a test compound; and determining the effect of the test compound on a contractile function in the presence and absence of the test compound, wherein a modulation of the contractile function in the presence of the test compound as compared to the contractile function in the absence of the test compound indicates that the test compound modulates a contractile function, thereby identifying a compound useful for treating or preventing a muscle disease.

In one embodiment, the contractile function is a biomechanical activity, e.g., a biomechanical activity selected from the group consisting of contractility, cell stress, cell swelling, and rigidity.

In another embodiment, the contractile function is an electrophysiological activity, e.g., a voltage parameter selected from the group consisting of action potential, action potential duration (APD), conduction velocity (CV), refractory period, wavelength, restitution, bradycardia, tachycardia, and reentrant arrhythmia; or a calcium flux parameter selected from the group consisting of intracellular calcium transient, transient amplitude, rise time (contraction), decay time (relaxation), total area under the transient (force), restitution, focal and spontaneous calcium release.

In one embodiment, the methods of the invention further include applying a stimulus to the plurality of muscle thin films.

In another embodiment, the plurality of muscle thin films are adhered to a solid support structure, e.g., a Petri dish, a multi-well plate, or a glass cover-slip.

In yet another embodiment, the plurality of muscle thin films are cultured in the presence of a fluorophore, such as a voltage-sensitive dye or an ion-sensitive dye. The voltage-sensitive dye may be an electrochromic dye (e.g., a styryl dye and a merocyanine dye). The ion-sensitive dye may be a calcium sensitive dye (e.g., X-Rhod, aequorin, Fluo3, Fluo5, or Rhod2). In other embodiments, the fluorophore may be a dye pair selected from the group consisting of di-2-ANEPEQ and calcium green; di-4-ANEPPS and Indo-1; di-4-ANEPPS and Fluo-4; RH237 and Rhod2; and, RH-237 and Fluo-3/4.

In some embodiments, the plurality of muscle thin films comprises cardiomyocytes, vascular smooth muscle cells, smooth muscle cells or skeletal striated muscle cells.

In another aspect, the present invention provides a device for measuring a contractile function. The device includes a solid support structure (e.g., a Petri dish, a multi-well plate, or a glass cover-slip); a plurality of muscle thin films adhered to the solid support structure, wherein the plurality of muscle thin films each comprise a flexible polymer layer (e.g., a flexible polymer layer comprising polydimethylsiloxane) and a population of isolated cells (e.g., myocytes such as cardiomyocytes) seeded on the flexible polymer layer in a predetermined pattern, and wherein the cells form a tissue structure which can perform a contractile function. The plurality of muscle thin films may be adhered to the solid support structure directly or indirectly, e.g., via a plurality of posts attached to the solid support structure.

In a further aspect, the present invention provides a device for measuring a contractile function which includes a solid support structure (e.g., a Petri dish, a multi-well plate, or a glass cover-slip); a plurality of muscle thin films adhered at one end to the solid support structure, wherein the plurality of muscle thin films comprise a flexible polymer layer (e.g., a flexible polymer layer comprising polydimethylsiloxane) and a population of isolated cells (e.g., myocytes such as cardiomyocytes) seeded on the flexible polymer layer in a predetermined pattern, wherein the cells form a tissue structure which can perform a contractile function. The myocytes may be aligned to produce an anisotropic tissue.

In one embodiment, the devices of the invention may comprise a second solid support structure seeded with a second population of cells.

In another embodiment, the flexible polymer layer is supplied with an engineered surface chemistry before the cells are seeded. The engineered surface chemistry may include an extracellular matrix protein. In other embodiments, the engineered surface chemistry is provided in a pattern that includes gaps.

In a further embodiment, the solid support structure includes a plurality of cell culture wells; an optical signal capture device; and an image processing software to calculate change in an optical signal. The optical signal capture device may further include fiber optic cables in contact with the culture wells.

In another aspect, the present invention provides methods of preparing a device suitable for measuring a contractile function. The methods include providing a solid support structure; coating a sacrificial polymer layer on the solid support structure; coating a flexible polymer layer that is more flexible than the support structure on the sacrificial polymer layer, wherein the flexible polymer layer does not cover the edges of the solid support structure; seeding cells on the flexible polymer layer; culturing the cells to form a tissue; and removing a portion of the formed tissue thereby generating strips of the formed tissue adhered at one end to the solid support structure, thereby preparing a device suitable for measuring a contractile function.

The present invention is further illustrated by the following detailed description and drawings.

BRIEF DESCRIPTION OF THE DRAWINGS

FIG. 6(A) depicts imaging and mapping of all the wells of a multi-well plate assay at once and FIG. 6(B) depicts imaging and mapping of each well of a multi-well plate assay individually.

FIG. 9A schematically depicts an embodiment of the fabrication of a horizontal MTF device using the protective film procedure in a multi-well dish with a zoomed in view of the film inside a well (not to scale).

FIG. 9B is a photo of a 24-well plate containing a checkered pattern of buffer with phenol red (grey) and without phenol red (white) used to detect leaks between wells.

FIG. 9C is a photo of a muscle thin film inside of a well of the 24-well plate depicted in FIG. 9B.

DETAILED DESCRIPTION OF THE INVENTION

Figure 1:
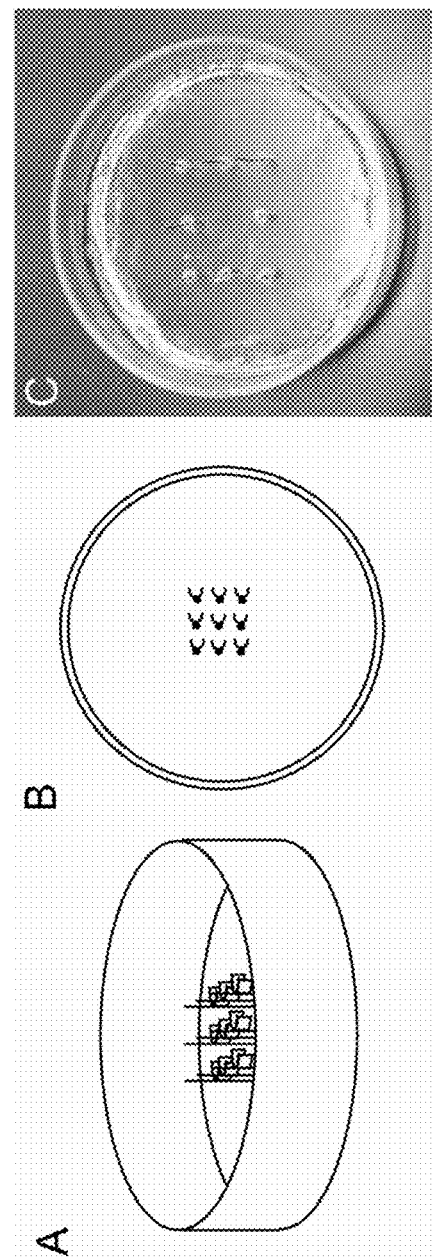
FIG. 1 depicts a device of the invention in which a homogeneous cell population is used. (A, B) Schematic representations of the device, with thin polymer films adhered to posts. (C) Photograph of the same device.

Described herein are methods and devices for multiplex and high throughput measurements of various properties of in vitro tissue constructs, e.g., for simultaneous or high-speed serial analysis of numerous samples. The devices and methods of the present invention can be used to measure muscle activities or functions, e.g., biomechanical forces that result from stimuli that include, but are not limited to, muscle cell contraction, osmotic swelling, structural remodeling and tissue level pre-stress. The devices and methods of the present invention may also be used for the evaluation of muscle activities or functions, e.g., electrophysiological responses, in a non-invasive manner, for example, in a manner that avoids cell damage. The devices and methods of the present invention are also useful for investigating muscle cell developmental biology and disease pathology, as well as in drug discovery and toxicity testing.

I. Devices of the Invention and Methods of Production of the Same

In one aspect, the present invention provides devices, e.g., devices for measuring a contractile function, which comprise a solid support structure, a plurality of muscle thin films (MTFs) adhered to the solid support structure, wherein the plurality of muscle thin films each comprise a flexible polymer layer and a population of isolated cells seeded on the flexible polymer layer in a predetermined pattern, and wherein the cells form a tissue structure which can perform a contractile function. The MTFs may be adhered to the solid support structure directly or indirectly, e.g., via the use of a post (e.g., the middle of an MTF is adhered to the post, as described in further detail below). One end (as in FIG. 6A) or both ends of the MTFs may be adhered to the solid support structure.

In one embodiment, the MTFs that are used in the devices and methods of the present invention may be prepared as described in PCT Publication No. WO 2008/051265, the entire contents of which are incorporated herein by reference. Briefly, substrates or devices for use in the methods of the invention are fabricated as a rigid base material coated with a sacrificial polymer layer; a flexible polymer layer is temporarily bonded to the rigid base material via the sacrificial polymer layer, and an engineered surface chemistry is provided on the flexible polymer layer to enhance or inhibit cell and/or protein adhesion. Cells are seeded onto the flexible polymer layer, and cultured to form a tissue comprising, for example, patterned anisotropic myocardium. A desired shape of the flexible polymer layer can then be cut; and the flexible film, including the polymer layer and tissue, can be peeled off with a pair of tweezers as the sacrificial polymer layer dissolves to release the flexible polymer layer, to produce a free-standing film.

The base layer may be formed of a rigid or semi-rigid material, such as a plastic, metal, ceramic, or a combination thereof. In one embodiment, the base layer is transparent so as to facilitate observation. In another embodiment, the base layer is opaque (e.g., light-absorbing). In one embodiment, a portion of the base layer is transparent (i.e., a portion underneath a portion of the MTF) and the remaining portion is opaque. In yet another embodiment, the base layer is translucent. The base layer is ideally biologically inert, has low friction with the tissues and does not interact (e.g., chemically) with the tissues. Examples of materials that can be used to form the base layer include polystyrene, polycarbonate, polytetrafluoroethylene (PTFE), polyethylene terephthalate, quartz, silicon, and glass. In one embodiment, the base layer is a silicon wafer, a glass cover slip, a multi-well plate, a tissue culture plate, a Petri dish, or a microfluidic chamber.

In one embodiment, the base layer and the solid support structure are the same. For example, as described below, a MTF may be fabricated on, for example, a glass cover-slip (the base layer) and subsequent to coating a flexible polymer layer ont the sacrificial polymer layer, the rigid base material is cut into sections. Such sections may be placed in, for example, a multi-well plate or a microfluidic chamber.

In another embodiment, the solid support structure and the base layer are different. For example, as described below, a MTF may be fabricated on, for example, a glass cover-slip (the base layer) which is subsequently cut into strips and applied to a solid support structure, such as a post adhered to a Petri-dish or a microfluidic chamber.

The sacrificial polymer layer is deposited on the base layer, i.e., is placed or applied onto the base layer. Depositing may include, but is not limited to, spraying, dip casting, and spin-coating. The sacrificial polymer layer may be deposited on substantially the entire surface or only a portion of the surface of the base layer.

In one embodiment, spin-coating is used to deposit the sacrificial polymer layer on the base material. "Spin-coating" is a process wherein the base layer is mounted to a chuck under vacuum and is rotated to spin the base layer about its axis of symmetry while a liquid or semi-liquid substance, e.g. a polymer, is dripped onto the base layer. Centrifugal force generated by the spin causes the liquid or semi-liquid substance to spread substantially evenly across the surface of the base layer.

In one embodiment, the sacrificial polymer is a thermally sensitive polymer that can be melted or dissolved to release the flexible polymer layer. For example, linear non-cross-linked poly(N-Isopropylacrylamide) (PIPAAM), which is a solid when dehydrated or at about 37° C., wherein the polymer is hydrated, but relatively hydrophobic. When the temperature of the polymer is dropped to about 35° C. or less, wherein the polymer is hydrated, but relatively hydrophilic, the polymer liquefies, thereby releasing the patterned flexible polymer layer (Feinberg et al., Science 317:1366-1370, 2007).

In another embodiment, the sacrificial polymer becomes hydrophilic when the temperature is lowered, thereby releasing hydrophobic coatings. For example, the sacrificial polymer can be hydrated, cross-linked PIPAAM, which is hydrophobic at about 37° C. and hydrophilic at about 35° C. or less (e.g., about 35° C. to about 32° C.). In yet another embodiment, the sacrificial polymer is an electrically actuated polymer that becomes hydrophilic upon application of an electric potential and releases a hydrophobic structure coated thereon. Examples of such a polymer include poly (pyrrole)s, which are relatively hydrophobic when oxidized and hydrophilic when reduced. Other examples of polymers that can be electrically actuated include poly(acetylene)s, poly(thiophene)s, poly(aniline)s, poly(fluorene)s, poly(3-hexylthiophene), polynaphthalenes, poly(p-phenylene sulfide), and poly(para-phenylene vinylene)s. In another embodiment, the sacrificial polymer is a degradable biopolymer that can be dissolved to release a structure coated thereon. For example, the polymer (e.g., polylactic acid, polyglycolic acid, poly(lactic-glycolic) acid copolymers, or nylons) undergoes time-dependent degradation by hydrolysis or by enzymatic action (e.g., fibrin degradation by plasmin, collagen degradation by collagenase, fibronectin degradation by matrix metalloproteinase).

In one embodiment, the sacrificial polymer is an ultra-hydrophobic polymer with a surface energy lower than the flexible polymer layer adhered to it. In this case, mild mechanical agitation will "pop" the patterned flexible polymer layer off of sacrificial polymer layer. Examples of such a polymer include but are not limited to alkylsilanes (octadecyltrichiorosilane and isobutyltrimethoxysilane), fluoroalkylsilanes (tridecafluorotetrahydrooctyltrichiorosilane, trifluoropropyltrichiorosilane and heptadecafluorotetrahydrodecyltrichlorosilane), silicones (methyihydrosiloxane-dimethylsiloxane copolymer, hydride terminated polydimethylsiloxane, trimethylsiloxy terminated polydimethylsiloxane and diacetoxymethyl terminated polydimethylsiloxane), fluorinated polymers (polytetrafluoroethylene, perfluoroalkoxy and fluorinated ethylene propylene). For example, the base material can be a glass cover slip coated with a sacrificial polymer layer of PIPAAM.

Examples of the elastomers that can be used to form the flexible polymer layer include polydimethylsiloxane (PDMS) and polyurethane. In one embodiment, the PDMS, once cured is opaque (e.g., light-absorbing). In other embodiments, thermoplastic or thermosetting polymers are used to form the flexible polymer layer. Alternative non-degradable polymers include polyurethanes, silicone-urethane copolymers, carbonate-urethane copolymers, polyisoprene, polybutadiene, copolymer of polystyrene and polybutadiene, chloroprene rubber, Polyacrylic rubber (ACM, ABR), Fluorosilicone Rubber (FVMQ), Fluoroelastomers, Perfluoroelastomers, Tetrafluoro ethylene/propylene rubbers (FEPM) and Ethylene vinyl acetate (EVA). In still other embodiments, biopolymers, such as collagens, elastins, polysaccharides, and other extracellular matrix proteins, are used to form the flexible polymer layer. Suitable biodegradable elastomers include hydrogels, elastin-like peptides, polyhydroxyalkanoates and poly(glycerol-sebecate). Suitable non-elastomer, biodegrable polymers include polylactic acid, polyglycolic acid, poly lactic glycolic acid copolymers.

In one embodiment, the flexible polymer layer comprises polydimethylsiloxane (PDMS). Thickness of the PDMS layer can be controlled by the viscosity of the prepolymer and by the spin-coating speed, ranging from 14 to 60 nm thick after cure. The viscosity of the prepolymer increases as the cross-link density increases. This change in viscosity between mixing and gelation can be utilized to spin-coat different thicknesses of flexible polymer layers. Alternatively the spin-coating speed can be increased to create thinner polymer layers. After spin-coating, the resulting polymer scaffolds are either fully cured at room temperature (generally, about 22° C.) or at 65° C.

In one embodiment, polymeric fibers prepared as described in U.S. Provisional Application No. 61/177,894, entitled "Methods and Devices for the fabrication of 3D Polymeric Fibers", filed, May 12, 2009, (the entire contents of which are incorporated herein by reference) may be used as for the sacrificial polymer layer and/or the flexible polymer layer.

In one embodiment, fluorescent beads, e.g., fluorospheres, are mixed with the flexible polymer layer prior to spin-coating the flexible polymer layer onto the sacrificial polymer layer.

The flexible polymer layer is then uniformly or selectively patterned with engineered surface chemistry to elicit (or inhibit) specific cell growth and function. The engineered surface chemistry can be provided via exposure to ultraviolet radiation or ozone or via acid or base wash or plasma treatment to increase the hydrophilicity of the surface.

A specific biopolymer (or combination of biopolymers) may be selected to recruit different integrins, or an engineered surface chemistry may be fabricated on the flexible polymer layer to enhance or inhibit cell and/or protein adhesion. The specific type of biopolymer used and geometric spacing of the patterning will vary with the application. In one embodiment, the engineered surface chemistry comprises a biopolymer, such as an ECM protein, to pattern specific cell types. The ECM may comprise fibronectin, laminin, one or more collagens, fibrin, fibrinogen, or combinations thereof. In one embodiment, the ECM is not uniformly distributed on the surface of the flexible polymer, but rather is patterned spatially using techniques including, but not limited to, soft lithography, self assembly, printed on the solid support structure with a polydimethylsiloxane stamp, vapor deposition, and photolithography. In one embodiment, the methods of the invention further comprise printing multiple biopolymer structures, e.g., the same or different, with successive, stacked printings. Additional suitable surface chemistries are provided in PCT Publication No. WO 2008/051265.

In one embodiment of the invention, a MTF is engineered using alternating high density lines of ECM protein with either low density ECM protein or a chemical that prevents protein adhesion (e.g., Pluronics F127). The spacing of these lines is typically 20 μm width at 20 μm spacing, (Feinberg, *Science* 317:1366-1370, 2007), however, the width and spacing may be altered to change the alignment. Changes in alignment in turn affect anisotropy and anisotropy ratio of the action potential propagation. The width and spacing of the ECM lines may be varied over the range from about 0.1 μm to about 1000 μm, from about 1 μm to about 500 μm, from about 1 μm to 250 μm, from about 1 μm to 100 μm, from about 1 μm to 90 μm, from about 1 μm to 80 μm, from about 1 μm to 70 μm, from about 1 μm to 60 μm, from about 1 μm to 50 μm, from about 1 μm to 40 μm, from about 1 μm to 30 μm, from about 1 μm to 20 μm, from about 1 μm to 10 μm, from about 2 μm to 100 μm, from about 2 μm to 90 μm, from about 2 μm to 80 μm, from about 2 μm to 70 μm, from about 2 μm to 60 μm, from about 2 μm to 50 μm, from about 2 μm to 40 μm, from about 2 μm to 30 μm, from about 2 μm to 20 μm, from about 2 μm to 10 μm, from about 1 μm to 100 μm, from about 5 μm to about 100 μm, from about 5 μm to about 90 μm, from about 5 μm to about 80 μm, from about 5 μm to about 70 μm, from about 5 μm to about 60 μm, from about 5 μm to about 50 μm, from about 5 μm to about 40 μm, from about 5 μm to about 30 μm, from about 5 μm to about 20 μm, and from about 5 μm to about 20 μm. The width and spacing of the ECM lines can be equivalent or disparate. For example, both the width and spacing can be about 0.1, about 0.2, about 0.25, about 5, about 0.75, about 1, about 2, about 3, about 4, about 5, about 6, about 7, about 8, about 9, about 10, about 11, about 12, about 13, about 14, about 5, about 16, about 17, about 18, about 19, or about 20 μm. In other embodiments, the width can be about 0.1, about 0.2, about 0.25, about 5, about 0.75, about 1, about 2, about 3, about 4, about 5, about 6, about 7, about 8, about 9, or about 10 μm and the spacing can be about 1, about 2, about 3, about 4, about 5, about 6, about 7, about 8, about 9, about 10, about 11, about 12, about 13, about 14, about 5, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, or about 40 μm. Conversely, the width can be about 1, about 2, about 3, about 4, about 5, about 6, about 7, about 8, about 9, about 10, about 11, about 12, about 13, about 14, about 5, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, or about 40 μm and the spacing can be about 0.1, about 0.2, about 0.25, about 5, about 0.75, about 1, about 2, about 3, about 4, about 5, about 6, about 7, about 8, about 9, or about 10 μm. Typically the patterned ECM lines are parallel to one another, but they may also be at angles to one another at about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90°. In one embodiment, the patterned ECM lines are parallel to one another at angles ranging from about 1° to about 90°. In another embodiment, the patterned ECM lines are parallel to one another at angles ranging from about 5° to about 45°. The angle between the patterned lines of ECM protein controls the directionality of action potential propagation. The width of the MTF itself can be tapered to control the direction of action potential propagation. For example, a wide MTF strip that tapers to a narrow strip will propagate an action potential from the wide to the narrow direction, but not in the opposite direction. Values and ranges intermediate to the above-recited values and ranges are also contemplated by the present invention.

In another embodiment, a MTF is engineered using stretching of, e.g., the flexible polymer layer during tissue formation. In one embodiment, the stretching is cyclic stretching. In another embodiment, the stretching is sustained stretching. In one embodiment, the flexible polymer layer is stretched at an appropriate time after cell seeding that is based on the type(s) of cells seeded. In one embodiment, the flexible polymer layer is stretched at about minutes, hours, or days after cell seeding onto a patterned flexible polymer layer. In one embodiment, the flexible polymer layer is stretched at about 0, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, or about 3.0 hours after cell seeding onto a patterned flexible polymer layer. In one embodiment, the flexible polymer layer is patterned isotropically. Stretching, therefore, results in the formation of anisotropic tissue, the anisotropy of which is in the direction of the stretch. In another embodiment, the flexible polymer layer is patterned anistropically and stretching enhances the anisotropy of the tissue formed.

In one embodiment, the flexible polymer layer is stretched using about a 0.1, 0.2, 0.3, 0.4, 0.5, 1.0, 1.5, 2.0, 2.5, 3.0, 3.5, 4, 4.5, 5.0, 5.5, or about 6.0, 6.5, 7.0, 7.5, 8.0, 8.5, 9.0, 9.5, or about 10.0 Hertz (Hz) cyclic stretch. In one embodiment, the flexible polymer layer is stretched using about 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, or about 20.0% strength sustained stretch.

To attach cells, substrates are placed in culture with a cell suspension allowing the cells to settle and adhere to the surface. In the case of an adhesive surface treatment, cells bind to the material in a manner dictated by the surface chemistry. For patterned chemistry, cells respond to patterning in terms of maturation, growth and function. Examples of cell types that may be used include contractile cells, such as, but not limited to, vascular smooth muscle cells, vascular endothelial cells, myocytes (e.g., cardiac myocytes), skeletal muscle, myofibroblasts, airway smooth muscle cells and cells that will differentiate into contractile cells (e.g., stem cells, e.g., embryonic stem cells or adult stem cells, progenitor cells or satellite cells).

The term "progenitor cell" is used herein to refer to cells that have a cellular phenotype that is more primitive (e.g., is at an earlier step along a developmental pathway or progression than is a fully differentiated cell) relative to a cell which it can give rise to by differentiation. Often, progenitor cells also have significant or very high proliferative potential. Progenitor cells can give rise to multiple distinct differentiated cell types or to a single differentiated cell type, depending on the developmental pathway and on the environment in which the cells develop and differentiate.

The term "progenitor cell" is used herein synonymously with "stem cell."

The term "stem cell" as used herein, refers to an undifferentiated cell which is capable of proliferation and giving rise to more progenitor cells having the ability to generate a large number of mother cells that can in turn give rise to differentiated, or differentiable daughter cells. The daughter cells themselves can be induced to proliferate and produce progeny that subsequently differentiate into one or more mature cell types, while also retaining one or more cells with parental developmental potential. The term "stem cell" refers to a subset of progenitors that have the capacity or potential, under particular circumstances, to differentiate to a more specialized or differentiated phenotype, and which retains the capacity, under certain circumstances, to proliferate without substantially differentiating. In one embodiment, the term stem cell refers generally to a naturally occurring mother cell whose descendants (progeny) specialize, often in different directions, by differentiation, e.g., by acquiring completely individual characters, as occurs in progressive diversification of embryonic cells and tissues. Cellular differentiation is a complex process typically occurring through many cell divisions. A differentiated cell may derive from a multipotent cell which itself is derived from a multipotent cell, and so on. While each of these multipotent cells may be considered stem cells, the range of cell types each can give rise to may vary considerably. Some differentiated cells also have the capacity to give rise to cells of greater developmental potential. Such capacity may be natural or may be induced artificially upon treatment with various factors. In many biological instances, stem cells are also "multipotent" because they can produce progeny of more than one distinct cell type, but this is not required for "stem-ness." Self-renewal is the other classical part of the stem cell definition. In theory, self-renewal can occur by either of two major mechanisms. Stem cells may divide asymmetrically, with one daughter retaining the stem state and the other daughter expressing some distinct other specific function and phenotype. Alternatively, some of the stem cells in a population can divide symmetrically into two stems, thus maintaining some stem cells in the population as a whole, while other cells in the population give rise to differentiated progeny only. Formally, it is possible that cells that begin as stem cells might proceed toward a differentiated phenotype, but then "reverse" and re-express the stem cell phenotype, a term often referred to as "dedifferentiation" or "reprogramming" or "retrodifferentiation".

The term "embryonic stem cell" is used to refer to the pluripotent stem cells of the inner cell mass of the embryonic blastocyst (see U.S. Pat. Nos. 5,843,780, 6,200,806, the contents of which are incorporated herein by reference). Such cells can similarly be obtained from the inner cell mass of blastocysts derived from somatic cell nuclear transfer (see, for example, U.S. Pat. Nos. 5,945,577, 5,994,619, 6,235,970, which are incorporated herein by reference). The distinguishing characteristics of an embryonic stem cell define an embryonic stem cell phenotype. Accordingly, a cell has the phenotype of an embryonic stem cell if it possesses one or more of the unique characteristics of an embryonic stem cell such that that cell can be distinguished from other cells. Exemplary distinguishing embryonic stem cell characteristics include, without limitation, gene expression profile, proliferative capacity, differentiation capacity, karyotype, responsiveness to particular culture conditions, and the like.

The term "adult stem cell" or "ASC" is used to refer to any multipotent stem cell derived from non-embryonic tissue, including fetal, juvenile, and adult tissue. Stem cells have been isolated from a wide variety of adult tissues including blood, bone marrow, brain, olfactory epithelium, skin, pancreas, skeletal muscle, and cardiac muscle. Each of these stem cells can be characterized based on gene expression, factor responsiveness, and morphology in culture. Exemplary adult stem cells include neural stem cells, neural crest stem cells, mesenchymal stem cells, hematopoietic stem cells, and pancreatic stem cells.

In one embodiment, progenitor cells suitable for use in the claimed devices and methods are Committed Ventricular Progenitor (CVP) cells as described in PCT Application No. PCT/US09/060224, entitled "Tissue Engineered Myocardium and Methods of Productions and Uses Thereof", filed Sep. 28, 2009, the entire contents of which are incorporated herein by reference.

The cells on the substrates are cultured in an incubator under physiologic conditions (e.g., at 37° C.) until the cells form a two-dimensional (2D) tissue (i.e., a layer of cells that is less than about 200 microns thick, or, in particular embodiments, less than about 100 microns thick, less than about 50 microns thick, or even just a monolayer of cells), the anisotropy or isotropy of which is determined by the engineered surface chemistry.

Any appropriate cell culture method may be used to establish the tissue on the polymer surface. The seeding density of the cells will vary depending on the cell size and cell type, but can easily be determined by methods known in the art. In one embodiment, cardiac myocytes are seeded at a density of between about $1 \times 10^5$ to about $6 \times 10^5$ cells/cm$^2$, or at a density of about $1 \times 10^4$, about $2 \times 10^4$, about $3 \times 10^4$, about $4 \times 10^4$, about $5 \times 10^4$, about $6 \times 10^4$, about $7 \times 10^4$, about $8 \times 10^4$, about $9 \times 10^4$, about $1 \times 10^5$, about $1.5 \times 10^5$, about $2 \times 10^5$, about $2.5 \times 10^5$, about $3 \times 10^5$, about $3.5 \times 10^5$, about $4 \times 10^5$, about $4.5 \times 10^5$, about $5 \times 10^5$, about $5.5 \times 10^5$, about $6 \times 10^5$, about $6.5 \times 10^5$, about $7 \times 10^5$, about $7.5 \times 10^5$, about $8 \times 10^5$, about $8.5 \times 10^5$, about $9 \times 10^5$, about $9.5 \times 10^5$, about $1 \times 10^6$, about $1.5 \times 10^6$, about $2 \times 10^6$, about $2.5 \times 10^6$, about $3 \times 10^6$, about $3.5 \times 10^6$, about $4 \times 10^6$, about $4.5 \times 10^6$, about $5 \times 10^6$, about $5.5 \times 10^6$, about $6 \times 10^6$, about $6.5 \times 10^6$, about $7 \times 10^6$, about $7.5 \times 10^6$, about $8 \times 10^6$, about $8.5 \times 10^6$, about $9 \times 10^6$, or about $9.5 \times 10^6$. Values and ranges intermediate to the above-recited values and ranges are also contemplated by the present invention.

In one embodiment, cardiac myocytes are co-cultured with neurons to prepare innervated engineered tissue comprising pacemaking cells, and/or to accelerate the maturation of the cultured cells as described in U.S. Provisional Application No. 61/306,736, the entire contents of which are incorporated herein by reference.

In one embodiment, a specific shape (e.g., a rectangular strip) is cut in the flexible polymer film using a scalpel, razor blade, punch, die or laser. The sacrificial layer is then dissolved or actuated to release the flexible polymer from the rigid base (e.g., by dropping the temperature below 35° C.); and the cut-out shape then floats free or is gently peeled off. The bending stiffness of the thin films along any given axis, much like a cantilever, increases with the elastic modulus, thickness and width while decreasing with length.

Suitable support structures for embodiments of the present invention include, for example, Petri dishes, cover-slips (circular or rectangular), strips of glass, glass slides, multi-well plates, microfluidic chambers, and microfluidic devices. The support structure is ideally biologically inert, it has low friction with the films and it does not interact (e.g., chemically) with the films. Examples of materials that can be used to form the support structure include polystyrene, polycarbonate, polytetrafluoroethylene (PTFE), polyethylene terephthalate, quartz, silicon (e.g., silicon wafers) and glass. In one embodiment, the support structure is transparent. In another embodiment, the support structure is opaque (e.g., light-absorbing). In one embodiment, a portion of the base layer is transparent (i.e., a portion underneath a portion of the MTF) and the remaining portion is opaque. In yet another embodiment, the base layer is translucent.

In one embodiment the base layer and the solid substrate are fabricated from the same material. In another embodiment, the base layer and the solid support are fabricated from different materials.

Examples of suitable materials for a co-culture device include, but are not limited to, tissue culture polystyrene, acid washed glass, extracellular matrix (e.g., collagen, fibronectin, fibrin, laminin) coated glass or polymer (e.g., PET, nylon), poly L-lysine coated glass or polymer.

In the embodiments of the invention in which the MTFs are attached to the solid support structure indirectly, via a post (as in FIGS. 1-3), the posts may be formed from a rigid material, such as polystyrene, stainless steel, polytetrafluoroethylene (PTFE) or a cactus needle. The post may also be adhesive to the thin film. In some embodiments, the post and film are mechanically adhesive (e.g., the film and post are clipped to each other).

Figure 3:
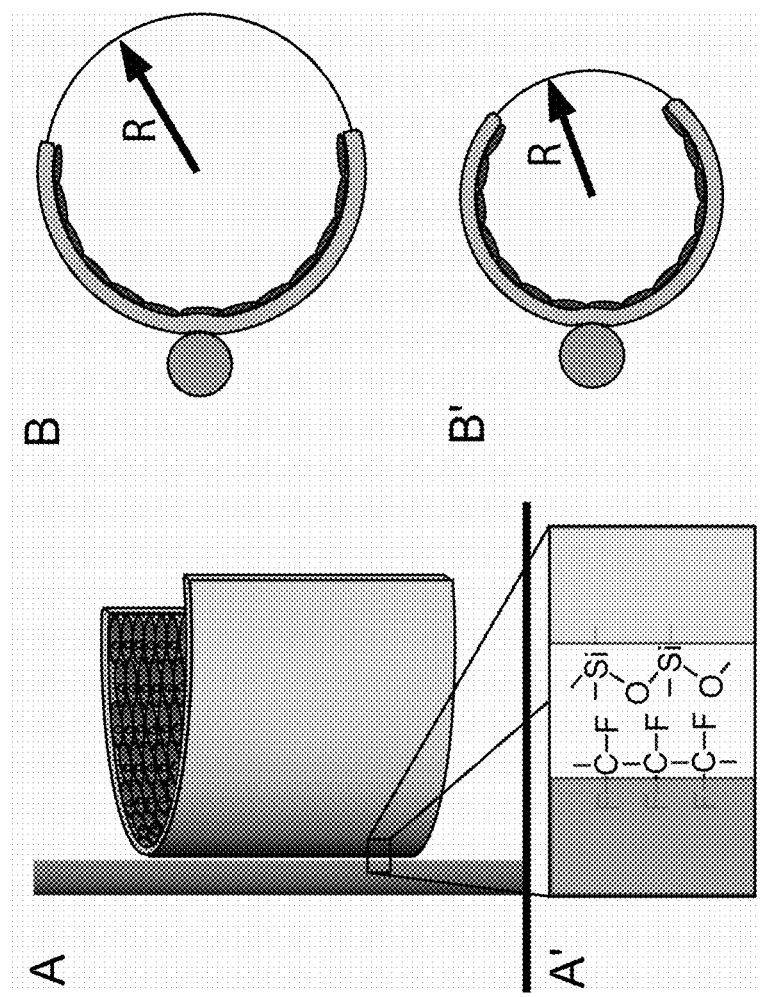
FIG. 3 provides illustrations of a thin film adhered to a post. (A) depicts the embodiment wherein the polymer side of thin film adheres to post. (A') depicts the embodiment wherein a PDMS thin film adheres to a PTFE post through hydrophobic-hydrophonic interaction. (B,B') depicts the embodiment wherein a change in the radius of curvature (R) can be used to calculate a change in stress in a cell layer.

In other embodiments, the post and film are chemically adhesive. For example, the post can be coated with adhesive glue. Alternatively, the post is coated or formed from a material that interacts with the flexible polymer layer of the film. For example, as shown in FIG. 3, the PDMS of the flexible polymer layer of the thin film adheres to a PTFE post through a hydrophobic-hydrophobic interaction. In other embodiments, the post may be coated with a material (e.g., poly L-lysine, collagen, fibronectin, fibrin, laminin) that binds to the cell layer of the thin film.

The appended Figures depict various embodiments of the devices of the present invention. For example, FIG. 1 depicts a device of the invention in which a homogeneous cell population is used. As shown in FIGS. 1A and 1B, schematic perspective and top views respectively, the system includes a solid support structure, such as a Petri dish, with posts affixed to it and substantially perpendicular to the base of the solid support structure. Thin films are adhered to the posts. A photograph of a device according to this embodiment is shown in FIG. 1C.

Figure 2:
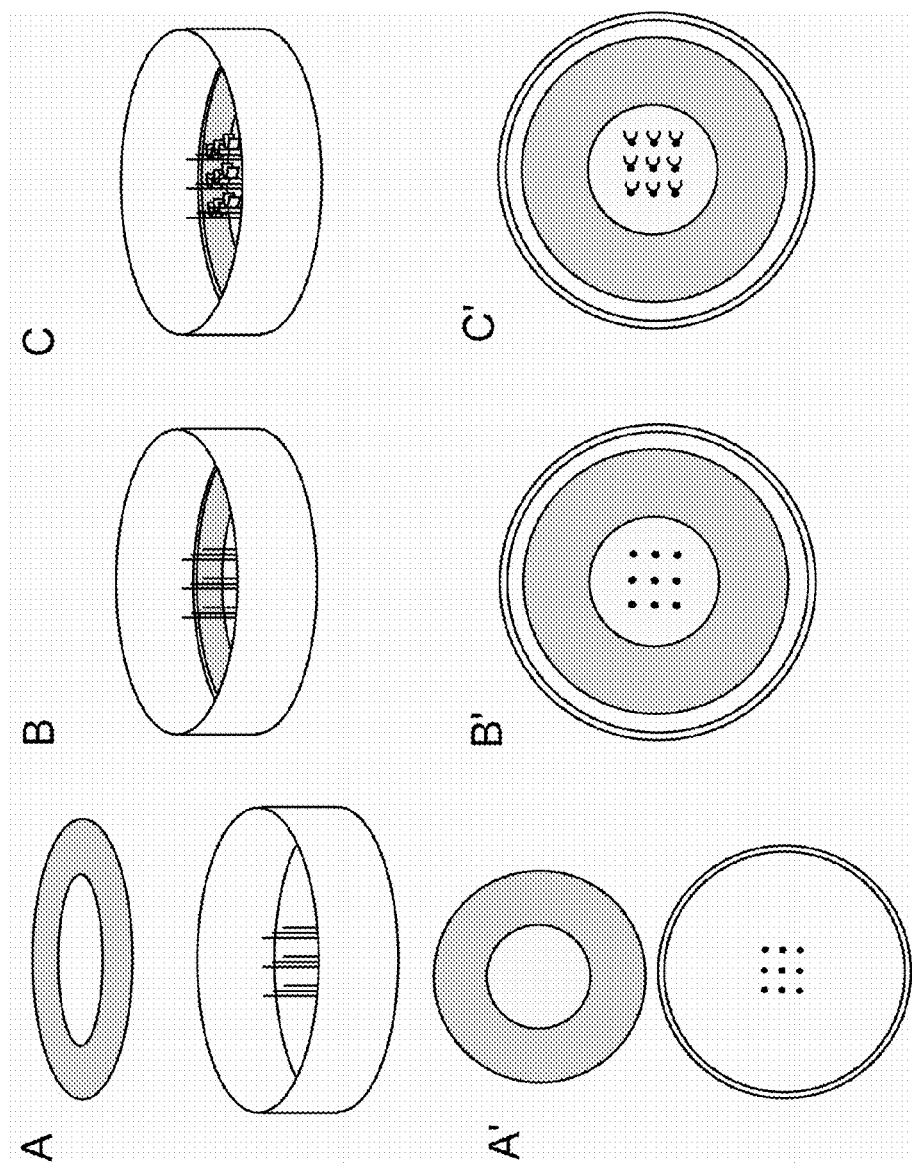
FIG. 2 depicts the system of FIG. 1 that further includes a co-culture slide. (A, A') depicts the embodiment wherein a co-culture slide is cultured separate from the device and (B, B') inserted into the device prior to performing the methods of the invention. (C, C') depicts the embodiment wherein the thin films are adhered to posts parallel to the dish base for optimal viewing.

FIG. 2 depicts a device of FIG. 1 that further includes a co-culture device, e.g., slide, that can be inserted into the assay dish. As shown in FIG. 2, the system includes a ring on which additional cells can be seeded, for the study of cell-cell interactions such as, for example, paracrine signaling. Cell-cell interactions, such as paracrine signaling can be studied by using films cultured with different cell types (e.g., vascular smooth muscle and cardiac myocytes) together. The use of thin films with different cell types together with a co-culture device allows for studies of three or more cell types.

Figure 4:
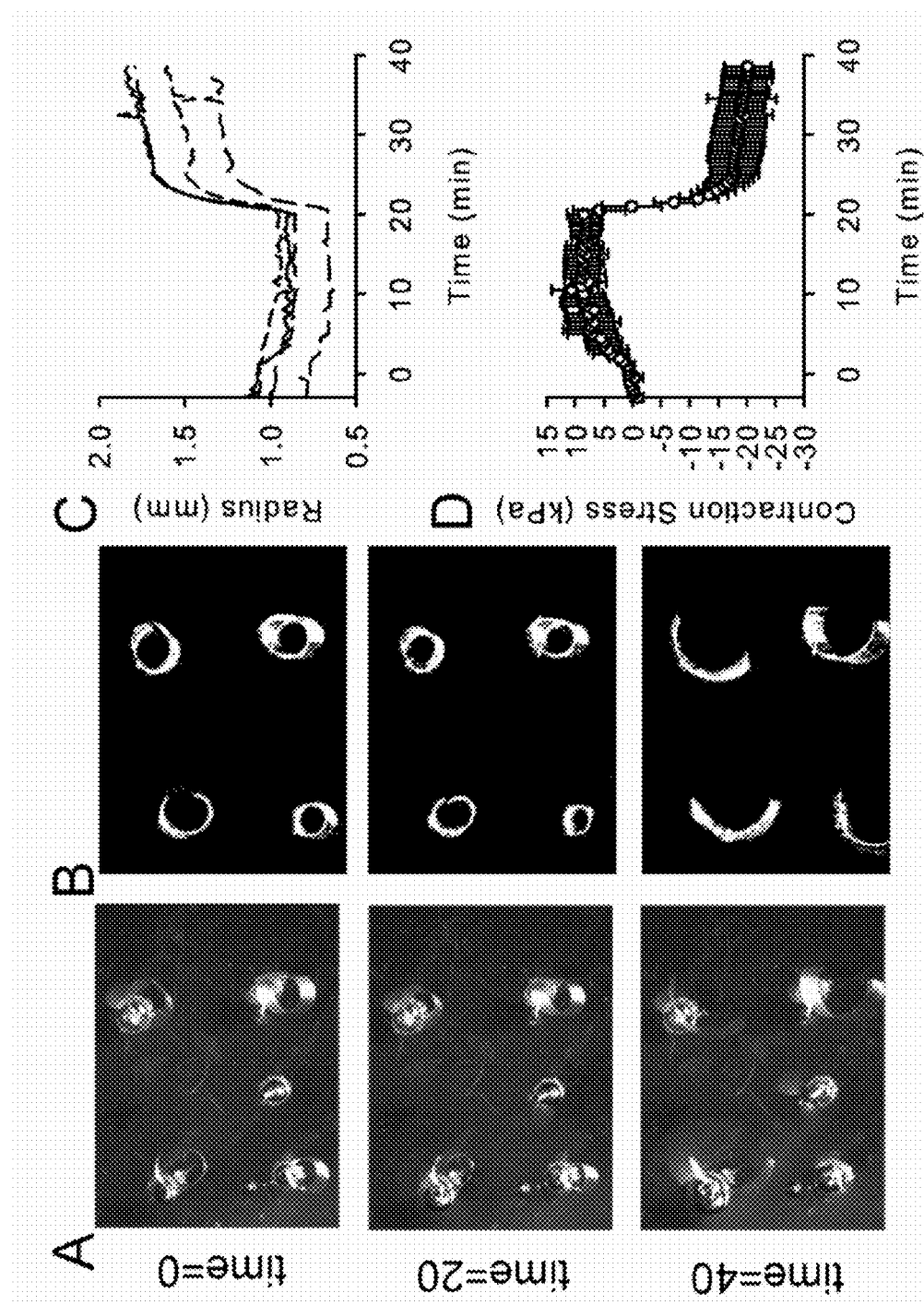
FIG. 4 provides images and charts of the system of FIG. 1 using rectangular-shaped muscular thin films with vascular smooth muscle anisotropically aligned along its length, and the deformation of the muscular thin films with time after treatment with endothelin-1. (A) depicts stereo microscopic images of polymeric thin films, seeded with vascular smooth muscle, adhered to posts. (B) depicts threshold images of thin films with films isolated from background. (C) depicts the measured change in radius of curvature with time. (D) depicts muscle stress necessary to induce change in curvature.

The devices of FIGS. 1 and 2 can be used as follows: When a co-culture device with secondary cells (e.g., aortic endothelial cells) is used, it is placed in the device, e.g., dish, in a buffered medium. Thin films are prepared and cut into strips, as discussed below or as described in PCT Publication No. WO 2008/051265. The strips are transferred to the device and are adhered to the posts such that the plane of primary curvature is parallel with the plane of the device, e.g., Petri dish base. A stimulus is applied to the films to cause stress in the cell layer. The curvature of the films is recorded and cell stress is calculated. A fluid perfusion system can be used to wash out test compounds that are being screened in a high throughput assay or to refresh the culture medium. A typical experiment using the device of FIG. 1 is shown in FIG. 4, where rectangular-shaped muscular thin films with vascular smooth muscle anisotropically aligned along their lengths were used, and the deformation of the muscular thin films with time after treatment with endothelin-1 was measured.

Figure 5:
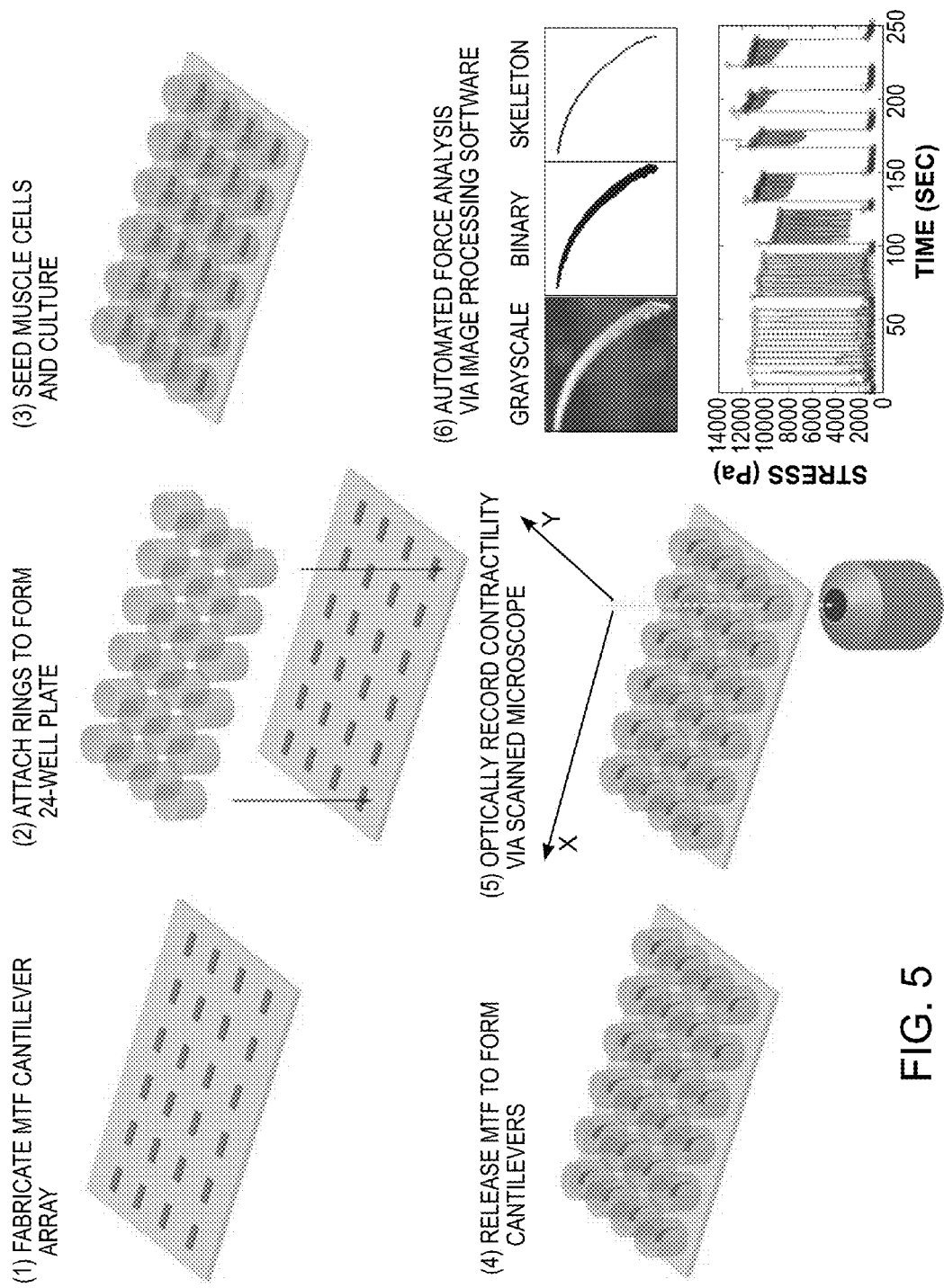
FIG. 5 schematically depicts the fabrication and use of a multi-well based device of the invention.
Figure 6:
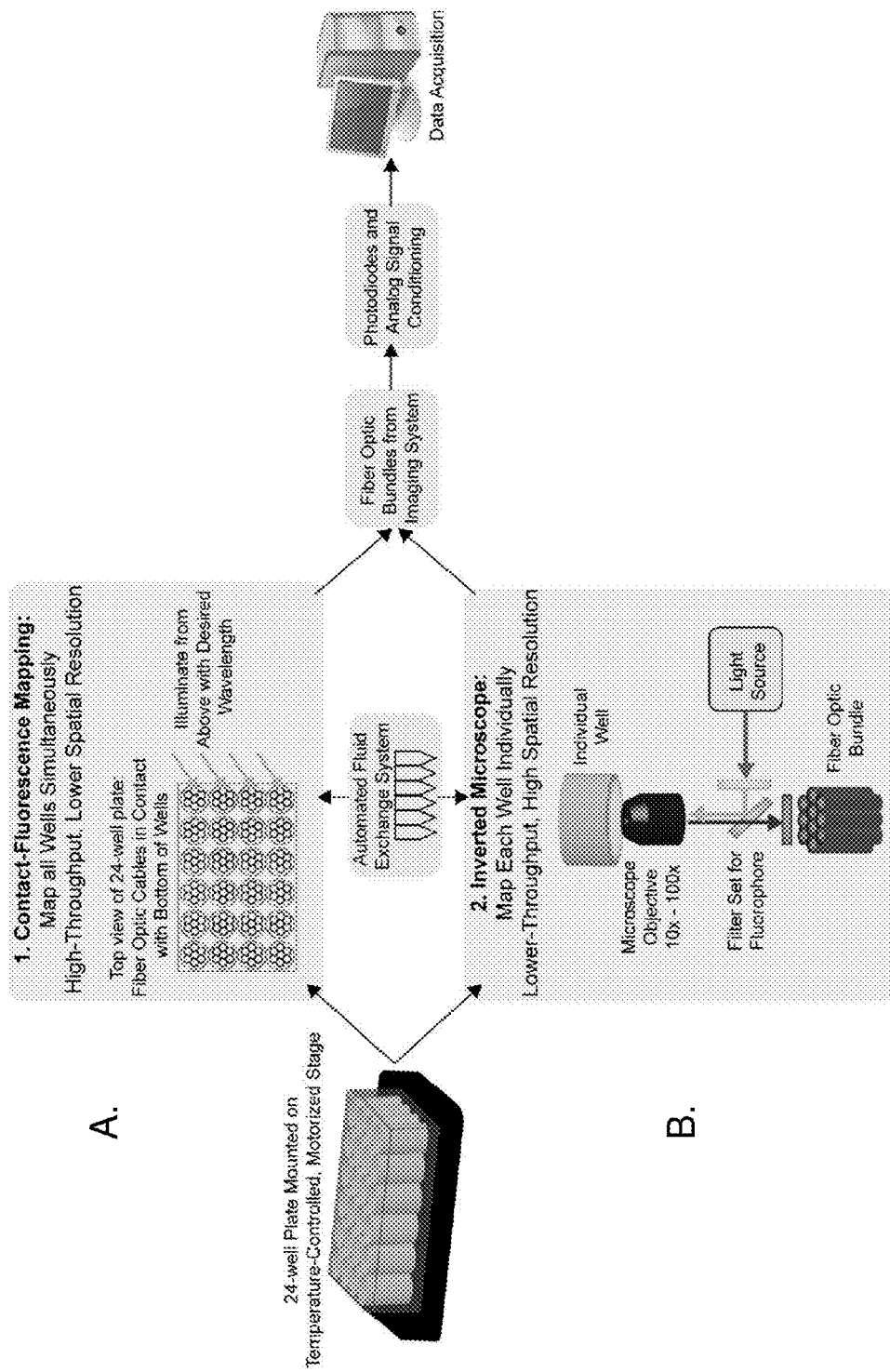
FIG. 6 graphically depicts two approaches for imaging the MTFs in the high-throughput methods described herein.

FIG. 5 schematically depicts one embodiment for the fabrication and use of a multi-well based device of the invention. According to this embodiment, an array of thin strips is created on a solid support structure. Rings are placed on the solid support structure creating a multi-well plate (e.g., about 8-, about 12-, about 16-, about 20-, about 24-, about 28-, about 32-about 36-, about 40, about 44, about 48-, about 96-, about 192-, about 384-wells) and isolating the strips. Cells are then seeded and cultured onto the strips to form tissue structures as described below or as described in PCT Publication No. WO 2008/051265. In one embodiment, cells are cultured in the presence of a fluorophore or fluorescent beads. One end of the strips is optionally detached from the solid support structure and released to form structures, e.g., cantilevers, which are free to deform when the tissue structures contract. The deformation (i.e., contractility) of the MTFs may be recorded, e.g., as depicted in FIG. 6. In the embodiment depicted in FIG. 6, contractility may be observed (and optionally recorded) using a microscope, which looks at one strip at a time while it scans across multiple samples (see FIG. 6B). In one embodiment of the invention, multiple strips are observed simultaneously (see FIG. 6A). Optionally, a lens is integrated into the platform. Changes in the curvature of the films are observed and the optical image is converted to a numerical value that corresponds to the curvature of the film. In one embodiment, a movie of MTF contractions in a multi-well dish is acquired (e.g., images are obtained in series). Images are processed and a mechanical analysis is optionally carried out to evaluate contractility. The output may be traction as a function of standard metrics such as peak systolic stress, peak upstroke power, upstroke time, and relaxation time.

Alternative ways of measuring bending of MTFs include, e.g., (i) using a laser bounced off of the thin film to record movement, (ii) using an integrated piezoelectric film in the MTF and recording a change in voltage during bending, (iii) integrating magnetic particles in the MTF and measuring the change in magnetic field during bending, (iv) placing a lens in the bottom of each well and simultaneously projecting multiple wells onto a single detector (e.g., camera, CCD or CMOS) at one time, (v) using a single capture device to sequentially record each well (see, e.g., FIG. 6(2)), e.g., the capture device is placed on an automated motorized stage. Finally, the measured bending information (e.g., digital image or voltage) is converted into force, frequency and other contractility metrics.

Figure 7A:
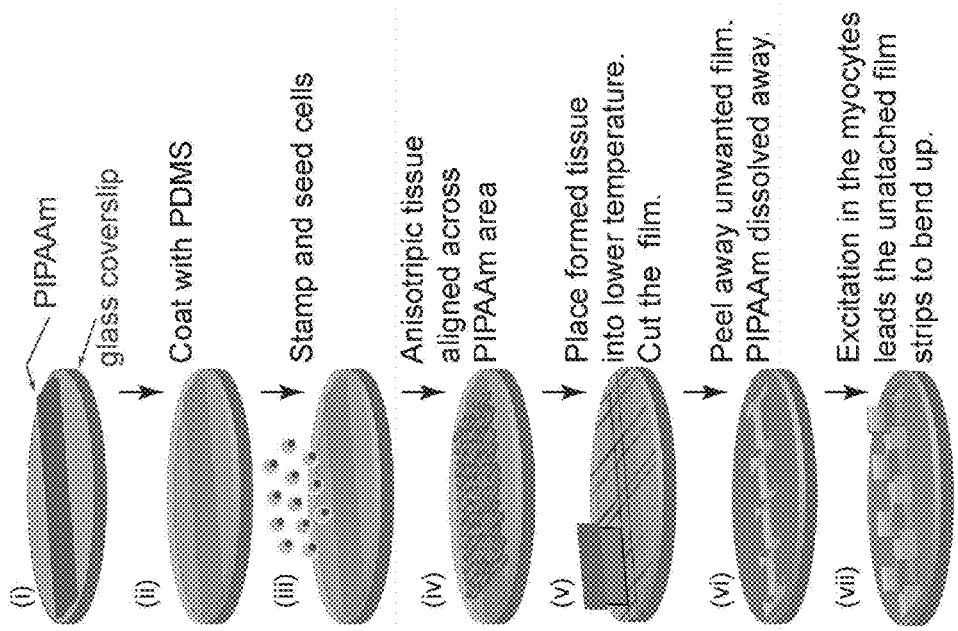
FIG. 7A schematically depicts one embodiment of the fabrication and use of a horizontal MTF device of the present invention.
Figure 7B:
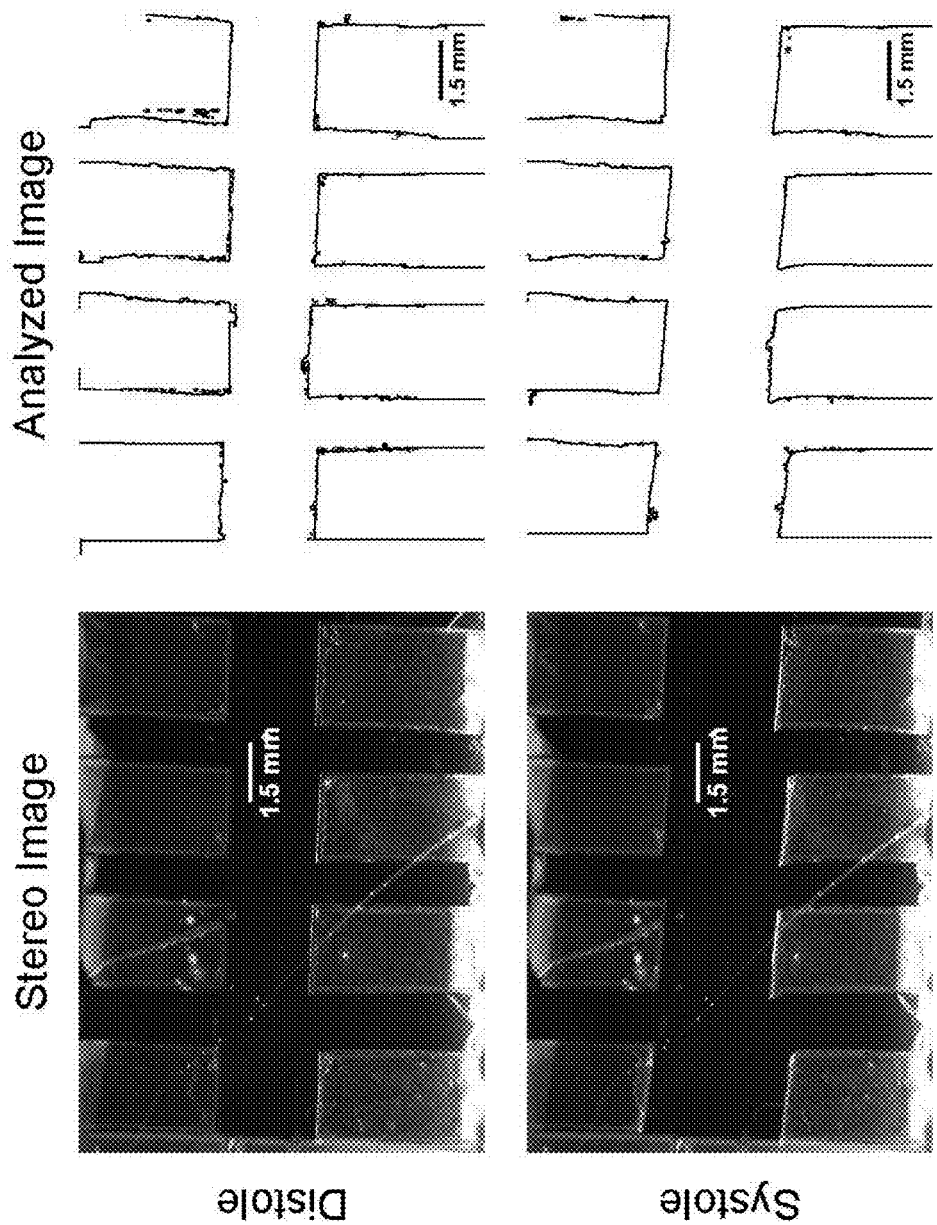
FIG. 7B is a photograph and image processing of the same device.
Figure 7C:
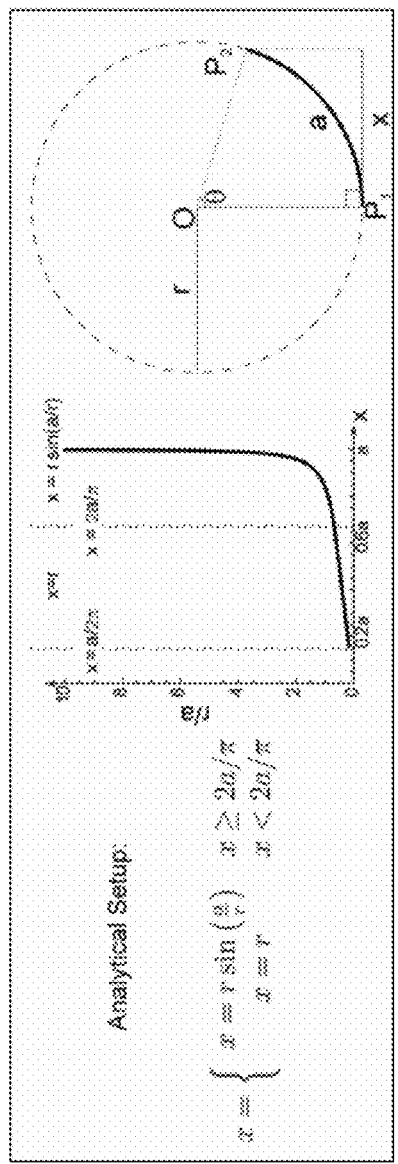
FIGS. 7C and 7D depict the calculation of the radius of curvature of the MTFs in the device depicted in FIG. 7A.

In another embodiment, as depicted in FIGS. 7A, 7B, and 7C, an MTF device is constructed horizontally rather than vertically such that handling of the MTF is not necessary allowing for increased throughput of MTF production. More specifically and similar to the MTF fabrication process described in WO 2008/051265, a substrate or device is fabricated as a rigid base material which is coated partially, i.e., all of the edges of the base material are not covered with a sacrificial polymer layer; a flexible polymer layer is temporarily bonded to the rigid base material via the sacrificial polymer layer, and an engineered surface chemistry is provided on the flexible polymer layer to enhance or inhibit cell and/or protein adhesion. Cells are seeded onto the flexible polymer layer and cultured to form a tissue. The formed tissue is then placed at a lower temperature (e.g., 35° C.)

In order to create the horizontal MTFs, sections of the flexible polymer layer can be cut and removed such that strips of the flexible film, including the polymer layer and tissue remain secured at their base to the base material and act as a hinge. This method allows the MTFs to curve upward off the base layer, i.e., to curve upward from the viewing (horizontal plane), as compared to the MTFs described above in which the MTF bends in the viewing plane) when stimulated to contract (see, e.g., FIGS. 1-3). In this embodiment, individual MTFs (e.g., 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100 or more MTFs) can be prepared on a single solid support structure, e.g., a glass cover slip (round or rectangular), a Petri dish, a glass slide, strips of glass, or a multi-well plate. The functional properties of these MTFs, e.g., the contractility of these MTFs, may be determined as described above for a vertical MTF.

Figure 8:
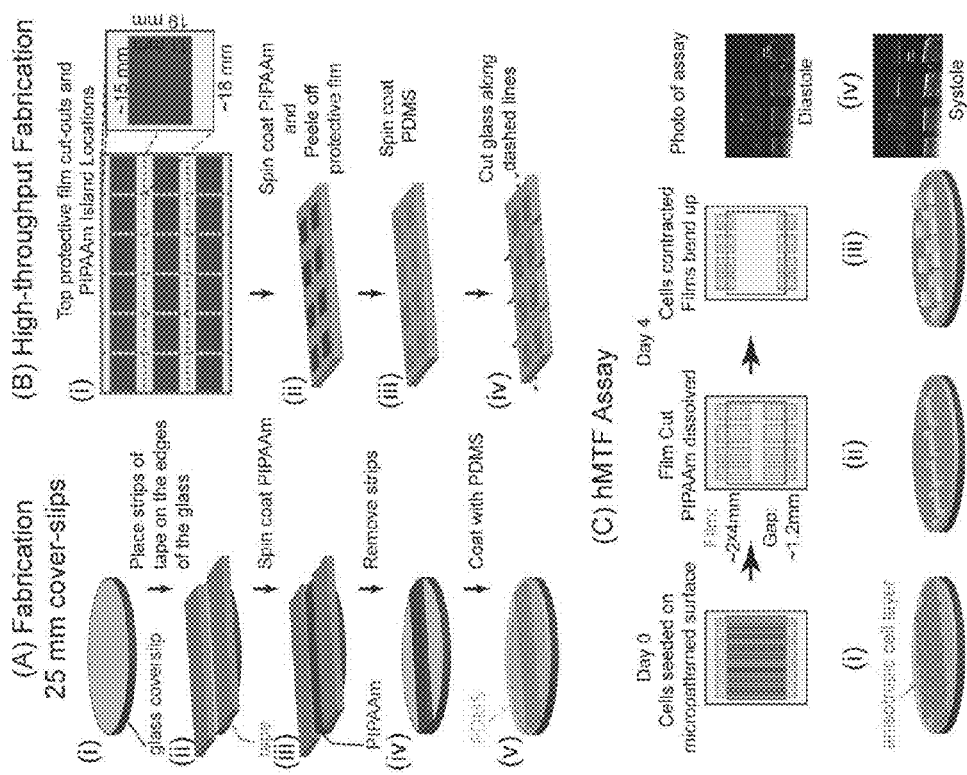
FIG. 8 schematically depicts the contrast between assaying contractility of an MTF using a large, rectangular glass comprising a horizontal MTF versus a round cover-slip comprising a horizontal MTF. (A) Fabication of a horizontal MTF using a round cover-slip; (B) Fabication of a horizontal MTF using a rectangular cover-slip (higher througput); (C) Contrast of running a contractility assay with a round cover-slip versus a square cover-slip. Although the manual fabrication of horizontal MTF is more efficient using square cover-slips, round cover-slips are often more compatible with commercially available microscope equipment.

In another embodiment, horizontal MTFs are fabricated as depicted in FIGS. 8A and 8B. More specifically, a protective film, e.g., static vinyl sheet or tape, e.g., adhesive tape, is applied to one or more portions of a rigid base material in order to prevent adherence of a sacrificial polymer to the rigid base material. The protective film may be applied to the rigid base material by, e.g., contacting the rigid base material with a liquid prior to applying the protective film to generate a liquid interface (e.g., any solvent that does not leave behind a residue on the rigid base material, e.g., ethanol) between the rigid base material and the protective film, and removing the excess liquid. In one embodiment, one or more portions of the top of the rigid base material (i.e., where the MTF will be formed) is coated with a protective film. In another embodiment, one or more portions, or all of the bottom (i.e., where the MTF will not be formed) of the rigid base material is coated with a protective film. In another embodiment, one or more portions of the top of the rigid base material and one or more portions or all of the bottom of the rigid base material are coated with a protective film.

In one embodiment, one or more sections of the protective film on the top surface of the rigid base material are cut and removed, thereby creating islands of rigid base material. The rigid base material partially coated with the protective film is then coated with a sacrificial polymer layer and the remaining protective film on the top of the rigid base material is removed. Subsequently, a flexible polymer layer is temporarily bonded to the rigid base material via the sacrificial polymer layer. If used, the bottom protective layer is then removed. Next, an engineered surface chemistry is provided on the flexible polymer layer to enhance or inhibit cell and/or protein adhesion, cells are seeded onto the flexible polymer layer and cultured to form a tissue, as described above. The formed tissue is then placed at a lower temperature (e.g., 35° C.) to dissolve the sacrificial polymer layer and sections of the flexible polymer layer (corresponding to the islands) can be cut to create the horizontal MTFs.

In one embodiment, the methods for fabricating a horizontal MTF (using a protective film described above), further comprise attaching a multi-well plate skeleton to the rigid base material subsequent to patterning the flexible polymer layer with an engineered surface chemistry and prior to cell seeding (see, e.g., FIG. 9A).

Figure 19:
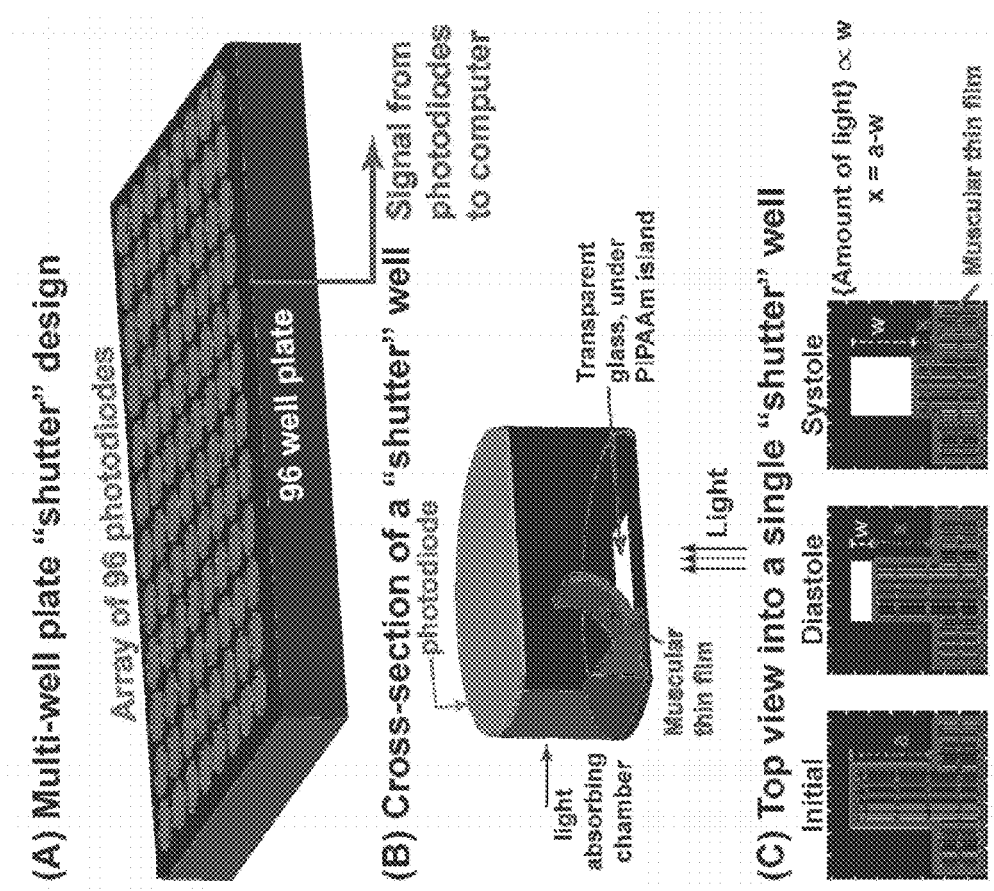
FIG. 19 schematically depicts an embodiment of the fabrication of a "shutter" horizontal MTF device in a multi-well dish. (A) A 96-well plate with a photodiode array top. Each photodiode measures, as a function of time, the amount of light emitted from each well, which holds a single horizontal MTF. The readouts of the photodiodes are transferred to a computer, where they are directly converted to a measurement of the radius of curvature, and muscle layer stress. (B) A cross-section of a single well with a "shutter design". The bottom of the plate is made from glass that has been blacked out except for a small area under the muscular thin film, which remains transparent to light. The muscular thin films are made from non-transparent bio-compatible polymers, i.e. black PDMS. The walls of the plate are made from black plastic, or other light absorbing material, to eliminate the reflection of light. During contraction of the cells, the thin film bends up from the glass uncovering a larger area of the transparent glass, allowing for a greater amount of light to pass through the chamber. The photodiode is located at the top of the well, where it collets light throughout the contraction cycle. (C) The top view into a single well of the "shutter system". This illustrates that the island of transparent glass has the same area as an unbent film (length a). As the film dissociates from the glass it bends up slightly during diastole, exposing some of the transparent glass. During the contraction the film bends up more, exposing more of the transparent glass. The amount of light reaching the photodiode will be proportional to the area of the white rectangle. As the width of the rectangle remains constant the signal is proportional to w which is simply the length of the film minus the x-projection. Therefore the signal transmitted from the photodiodes is proportional to the x-projection. Example 2 and FIG. 7C describe how to calculate the radius of curvature from measurements of the x-projection. However, the use of a photodiode array dispenses with the need for image analysis as the x-projection is a direct readout. This allows for this device to be an automated, high-throughput, simultaneous contraction measuring device.

In one embodiment, a device comprising a horizontal MTF and a multi-well plate further comprises a photodiode array (see, e.g., FIG. 19).

In one embodiment, as described above for a vertical MTF, the solid support structure may further comprise an optical signal capture device and an image processing software to calculate change in an optical signal. The optical signal capture device may further include fiber optic cables in contact with the device and/or a computer processor in contact with the device.

In one embodiment, an electrode is in contact with the device.

Figure 10:
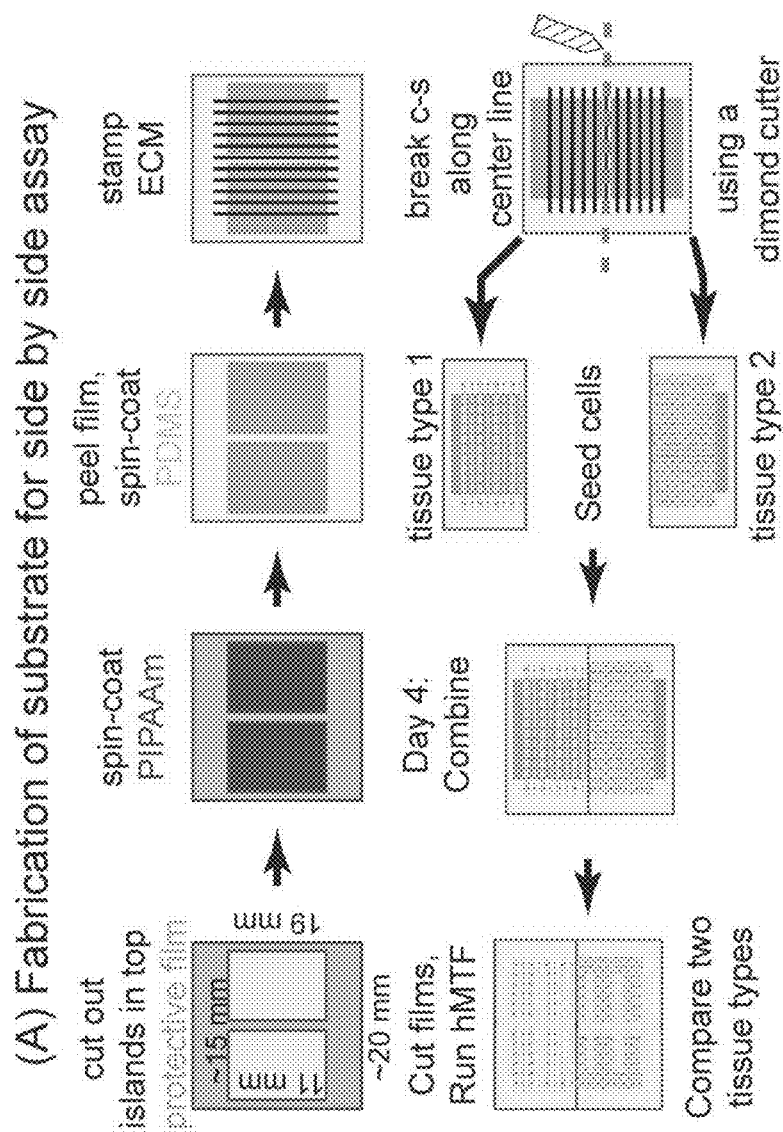
FIG. 10 schematically depicts one embodiment of the fabrication of a two tissue type horizontal MTF device useful for a side-by-side assay.
Figure 11:
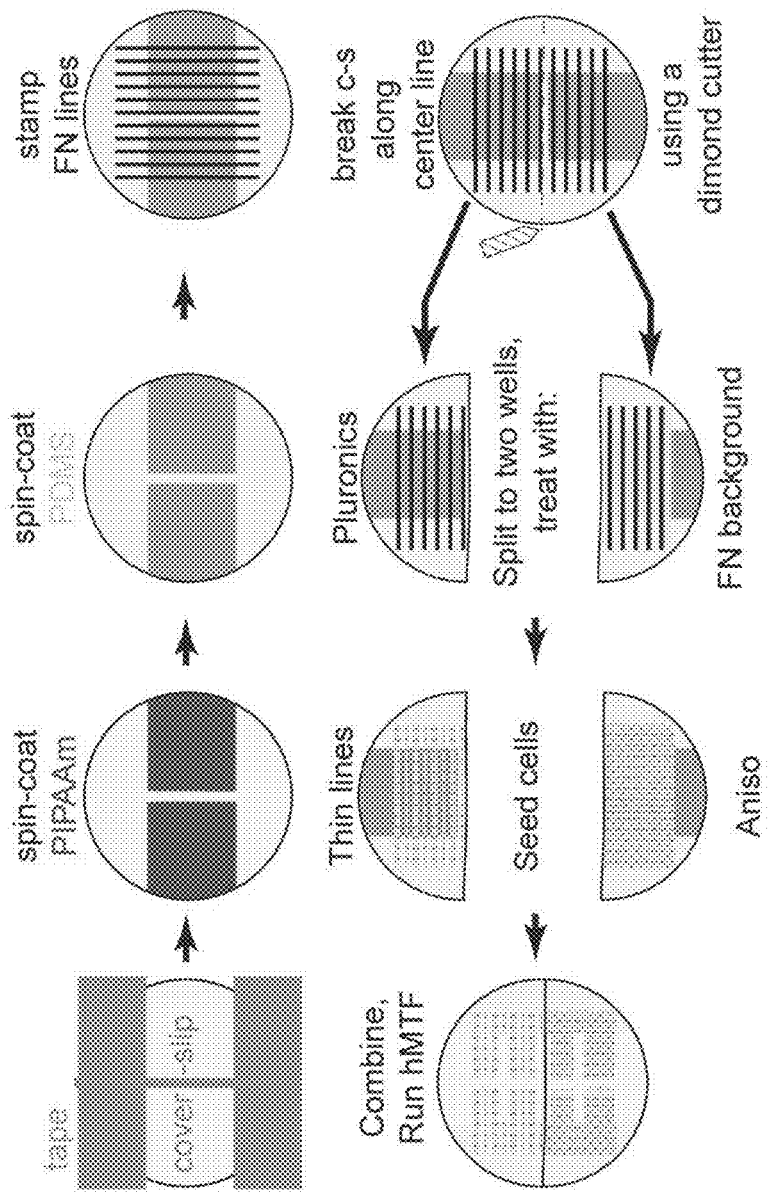
FIG. 11 schematically depicts another embodiment of the fabrication of a two tissue type horizontal MTF device useful for a side-by-side assay.

In certain embodiments of the invention, prior to patterning the flexible polymer layer with an engineered surface chemistry, the rigid base material coated with a sacrificial polymer layer and a flexible polymer layer, are divided, e.g., are cut, into portions, i.e., separate, individual devices (see, FIGS. 10 and 11). Such devices are useful for "side-by-side" assays that can be used, e.g., to qualitatively compare contractions of two tissue types, to compare the effect of one tissue response in proximity to another tissue, to compare biomechanical measurements of myocyte contraction properties, e.g., in response to various mechanical or chemical stimuli, to compare the effect of various patterning on tissue contractility, to compare different types of cells, or as an appropriate control. In other embodiments, the device is divided into individual devices prior to cell seeding and subsequent to patterning the flexible polymer layer with an engineered surface chemistry.

In one embodiment, devices that are divided subsequent to patterning the flexible polymer layer with an engineered surface chemistry may be further contacted with the same or different engineered surface chemistry to elicit or inhibit specific cell growth and/or function. In one embodiment, an individual device is combined with (e.g., placed in physical proximity to) one or more other individual devices subsequent to cell seeding such that the two devices share the same media and/or test compound and/or can send a paracrine signal. In one embodiment, two or more devices placed in physical proximity to each other are separated by a membrane which allows molecules of a certain size to pass through. In another embodiment, two or more devices are combined by a channel such that they share the same media and/or test compound but cannot send a paracrine signal.

In another embodiment, the invention provides a microfluidics device comprising a solid support structure which comprises a plurality MTF (i.e., the device comprises a plurality of microfluidic chambers each comprising a MTF), such as depicted in FIGS. 13, 14, 16, and 18B and described in, for example, PCT Publication Nos. WO 2010/042284, WO 2007/044888, and WO 2010/041230, the entire contents of each of which are incorporated herein by reference. In one embodiment, the plurality of microfluidic chambers comprising a MTF is operably connected to two or more inlet microchannels each comprising a valve, such as described in, for example, WO 2007/044888, to regulate flow, and two or more outlet microchannels.

In one embodiment, the two or more inlet microchannels comprise one or more mixing chambers (a section of the inlet microchannel that generates turbidity). Such devices may have 2-1002 microchambers comprising a MTF, and 2, 3, 4, 5, 6, 7, 8, 9, or 10 inlet microchannels, each with a valve. Such devices may have from 1-1000 mixing chambers. Such devices are useful for generating concentration gradients of a test compound to perform a dose response assay with the test compound. The number of concentrations of the test compound that may be produced in such a device is dependent on the number of mixing chambers.

In another embodiment, the plurality of microfluidic chambers comprising a MTF is operably connected to one or more inlet ports and does not comprise a mixing chamber. Such devices may comprise 1-1000 inlet ports and 1-1000 microchambers comprising a MTF. Such devices are also useful for performing a dose response assay with a test compound, however the various drug concentrations must be pre-mixed and introduced intoan inlet port separately.

In one embodiment, the microfluidics devices of the invention further optionally comprise one or more (e.g., 1, 2, 3, 4, 5, 6, 7, 8, 9, or 10) collection ports.

Fluid may be moved through the microfluidics devices by any suitable means, such as electrochemical or pressure-driven means.

A microfluidic chamber and a microfluidic channel may be fabricated into one or more materials including but not limited to, Polydimethylsiloxane (PDMS), polyurethanes, other elastomers, thermoplastics (e.g. polymethyl methacrylate (PMMA), polyethylene, polyethylene terephthalate, polystyrene), epoxies and other thermosets, silicon, silicon dioxide, and indium tin oxide (ITO).

Any suitable method may be used to fabricate a microfluidic channel and/or chamber, such as, for example, micromachining, injection molding, laser etching, laser cutting, and soft lithography. In one embodiment, an electrode is fabricated into a chamber using a non-reactive metal, such as, platinum, gold, and indium tin oxide.

A MTF suitable for use in a microfluidics device may be fabricated as described herein and in, for example PCT Publication No. WO 2008/051265, and cut into suitably sized strips. Alternatively, horizontal polymeric thin films may be fabricated as described herein. Cells may be seeded prior to assembly of the thin film into a microfluidics device and/or may be seeded subsequent to full assembly of the device. In addition, a polymeric thin film may be pre-fabricated into a chamber of the microfluidics device, or may be added to a chamber of the device after the device is fabricated.

The benefits of such a device for use in the methods of the invention include, for example, creation of a microenvironment that more closely resembles an in vivo fluidic microenvironment, increasing the number of assays that may be performed simultaneously while decreasing the amount of test compound required, ability to create a wide range of test compound concentrations for simultaneous assaying, and the ability to maintain MTFs in culture for up to one month in culture (depending on the tissue type).

In yet other embodiments of the invention, MTFs may be free floating. In one embodiment, MTFs are separated from the well edges by 1-2 lengths of the MTF.

In the embodiments of the invention where the solid support structure is a multi-well plate, each well may contain one MTF, two MTFs, or multiple MTFs.

In one embodiment, fluorescent beads, e.g., fluorospheres, are mixed with the flexible polymer layer prior to spin-coating the flexible polymer layer onto the sacrificial polymer layer. The addition of such beads may enhance data capture.

In certain embodiments of the invention, e.g., for evaluation of electrophysiological activities, cells are cultured in the presence of a fluorophor such as a voltage-sensitive dye or an ion-sensitive dye. For example, the voltage-sensitive dye is an electrochromic dye such as a styryl dye or a merocyanine dye. Exemplary electrochromic dyes include RH-421 or di-4-ANEPPS. Ion-sensitive, e.g., calcium sensitive dyes, include aequorin, Fluo3, and Rhod2. For simultaneous measurements of action potentials and intracellular calcium, the following exemplary dye pairs are used: di-2-ANEPEQ and calcium green; di-4-ANEPPS and Indo-1; di-4-ANEPPS and Fluo-4; RH237 and Rhod2; and, RH-237 and Fluo-3/4.

In such embodiments, the device includes MTFs grown in multi-well, e.g., 2-8-, 12-, 16-, 20-, 24-, 28-, 32-36-, 40, 44, 48-, 96-, 192-, 384-well, plates prepared as described herein. An inverted microscope or contact-fluorescence imaging system with temperature-controlled, humidity-controlled motorized may be used to monitor muscle activity, e.g., electrophysiological changes, such as action potentials and/ or intracellular calcium transients. An integrated fluid-handling system may also be used to apply/exchange fluorophores and test compounds, and a microfluidics chamber may be used for simulated drug delivery. The microfluidics chamber simulates microvasculature to mimic the manner in which a compound/drug contacts a target MTF comprising, e.g., cardiomyocytes. For example, an MTF may respond differently to a concentration gradient or different modes of administration. A significant advantage of the devices and systems described herein is that optical mapping system permits detection of such gradient effects, whereas earlier systems, e.g., single cell patch clamp studies, cannot measure gradient effects on a cell population.

Appropriate light source and filter sets may be chosen for each desired fluorophore based on the wavelength of the excitation light and fluoresced light of the fluorophore. Integration of excitation wavelength-switching or an additional detector permits ratiometric calcium imaging. For this purpose, exemplary fluorophores include Fura-2 and Indo-1 or Fluo-3 and Fura Red. For example, excitation and emission filters at 515±5 and >695 nm, respectively, are used to measure action potentials with di-4-ANEPPS, and excitation and emission filters at 365±25 and 485±5 nm, respectively, are used to measure calcium transients with Indo-1. Automated software may be used and customized for data acquisition and data analysis.

Advantages of the optical mapping system include non-invasiveness (no damage is inflicted to the cell membrane), recorded signals are real-time action potentials and/or calcium transients in contrast to derivatives of action potentials like extracellular recordings or slowly changing intracellular ionic concentrations or membrane potential like the FLIPR system.

For high-throughput optical mapping, analysis may be carried out using two different imaging approaches. For Contact Fluorescence Mapping, a microscope is not required. Fiber optic cables contact the bottom of a culture plate or wells of a multi-well plate containing MTFs. The plate or wells of the plate are then mapped based on the detected fluorescence. To screen compounds, test compounds are added to each individual well of a multi-well plate, and each bundle of fiber optic cables collects data from each different well providing data pertaining to MTF response to the test compound.

In another embodiment, an inverted microscope may be used to map each well individually. Cells of an MTF are contacted with, e.g., a chromophore, a fluorophor, or a bioluminescent material, and the microscope objective is moved from well to well to measure muscle activities or functions, e.g., electrophysiological changes. For example, the response of the MTF to each test compound is monitored for alterations in cardiac excitation, e.g., to identify drugs that induce or do not cause cardiac arrhythmia. Each of the approaches provides significant advantages (e.g., speed, efficiency, no or minimal user contact with the MTF, reduced user skill required, ability to observe and measure cell-cell interactions, ability to map action potential propagation and conduction velocity, and ability to observe and measure fibrillation and arrhythmia)) compared to previous assays used to measure electrophysiological changes (e.g., patch clamp assay in which a single cell is patch clamped).

These systems are well suited to screen test compounds for, for example, cardiac safety. For example, FDA Guideline S7B addresses "Safety pharmacology studies for assessing the potential for delayed ventricular repolarization by human pharmaceuticals". The devices and high-throughput in vitro assays described herein allow the identification of cardiac safety risks much earlier in the drug discovery process. The devices and methods of the invention are also useful for anti-arrhythmic and/or ion channel-targeted drug discovery.

II. Applications of the Devices of the Invention

The devices of the invention are useful for, among other things, measuring muscle activities or functions, investigating muscle developmental biology and disease pathology, as well as in drug discovery and toxicity testing.

Accordingly, the present invention also provides methods for identifying a compound that modulates a contractile function. The methods include providing a plurality of muscle thin films; contacting a plurality of the muscle thin films with a test compound; and determining the effect of the test compound on a contractile function in the presence and absence of the test compound, wherein a modulation of the contractile function in the presence of the test compound as compared to the contractile function in the absence of the test compound indicates that the test compound modulates a contractile function, thereby identifying a compound that modulates a contractile function.

In another aspect, the present invention also provides methods for identifying a compound useful for treating or preventing a muscle disease. The methods include providing a plurality of muscle thin films; contacting a plurality of the muscle thin films with a test compound; and determining the effect of the test compound on a contractile function in the presence and absence of the test compound, wherein a modulation of the contractile function in the presence of the test compound as compared to the contractile function in the absence of the test compound indicates that the test compound modulates a contractile function, thereby identifying a compound useful for treating or preventing a muscle disease.

The methods of the invention generally comprise determining the effect of a test compound on an MTF as a whole, however, the methods of the invention may comprise further evaluating the effect of a test compound on an individual cell type(s) of the MTF.

As used herein, the various forms of the term "modulate" are intended to include stimulation (e.g., increasing or upregulating a particular response or activity) and inhibition (e.g., decreasing or downregulating a particular response or activity).

As used herein, the term "contacting" (e.g., contacting a plurality of MTFs with a test compound) is intended to include any form of interaction (e.g., direct or indirect interaction) of a test compound and an MTF or a plurality of MTFs. The term contacting includes incubating a compound and an MTF or plurality of MTFs together (e.g., adding the test compound to an MTF or plurality of MTFs in culture).

Test compounds, may be any agents including chemical agents (such as toxins), small molecules, pharmaceuticals, peptides, proteins (such as antibodies, cytokines, enzymes, and the like), nanoparticles, and nucleic acids, including gene medicines and introduced genes, which may encode therapeutic agents, such as proteins, antisense agents (i.e., nucleic acids comprising a sequence complementary to a target RNA expressed in a target cell type, such as RNAi or siRNA), ribozymes, and the like.

The test compound may be added to an MTF by any suitable means. For example, the test compound may be added drop-wise onto the surface of a device of the invention and allowed to diffuse into or otherwise enter the device, or it can be added to the nutrient medium and allowed to diffuse through the medium. In the embodiment where the device of the invention comprises a multi-well plate, each of the culture wells may be contacted with a different test compound or the same test compound. In one embodiment, the screening platform includes a microfluidics handling system to deliver a test compound and simulate exposure of the microvasculature to drug delivery. In one embodiment, a solution comprising the test compound may also comprise fluorescent particles, and a muscle cell function may be monitored using Particle Image Velocimetry (PIV).

Numerous physiologically relevant parameters, e.g., muscle activities, e.g., biomechanical and electrophysiological activities, can be evaluated using the methods and devices of the invention. For example, in one embodiment, the devices of the present invention can be used in contractility assays for contractile cells, such as muscular cells or tissues, such as chemically and/or electrically stimulated contraction of vascular, airway or gut smooth muscle, cardiac muscle, vascular endothelial tissue, or skeletal muscle. In addition, the differential contractility of different muscle cell types to the same stimulus (e.g., pharmacological and/or electrical) can be studied.

In another embodiment, the devices of the present invention can be used for measurements of solid stress due to osmotic swelling of cells. For example, as the cells swell the MTF will bend and as a result, volume changes, force and points of rupture due to cell swelling can be measured.

In another embodiment, the devices of the present invention can be used for pre-stress or residual stress measurements in cells. For example, vascular smooth muscle cell remodeling due to long term contraction in the presence of endothelin-1 can be studied.

Further still, the devices of the present invention can be used to study the loss of rigidity in tissue structure after traumatic injury, e.g., traumatic brain injury. Traumatic stress can be applied to vascular smooth muscle thin films as a model of vasospasm. These devices can be used to determine what forces are necessary to cause vascular smooth muscle to enter a hyper-contracted state. These devices can also be used to test drugs suitable for minimizing vasospasm response or improving post-injury response and returning vascular smooth muscle contractility to normal levels more rapidly.

In other embodiments, the devices of the present invention can be used to study biomechanical responses to paracrine released factors (e.g., vascular smooth muscle dilation due to release of nitric oxide from vascular endothelial cells, or cardiac myocyte dilation due to release of nitric oxide).

In other embodiments, the devices of the invention can be used to evaluate the effects of a test compound on an electrophysiological parameter, e.g., an electrophysiological profile comprising a voltage parameter selected from the group consisting of action potential, action potential morphology, action potential duration (APD), conduction velocity (CV), refractory period, wavelength, restitution, bradycardia, tachycardia, reentrant arrhythmia, and/or a calcium flux parameter, e.g., intracellular calcium transient, transient amplitude, rise time (contraction), decay time (relaxation), total area under the transient (force), restitution, focal and spontaneous calcium release, and wave propagation velocity. For example, a decrease in a voltage or calcium flux parameter of an MTF comprising cardiomyocytes upon contacting the MTF with a test compound, would be an indication that the test compound is cardiotoxic.

In yet another embodiment, the devices of the present invention can be used in pharmacological assays for measuring the effect of a test compound on the stress state of a tissue. For example, the assays may involve determining the effect of a drug on tissue stress and structural remodeling of the MTF. In addition, the assays may involve determining the effect of a drug on cytoskeletal structure (e.g., sarcomere alignment) and, thus, the contractility of the MTF.

In still other embodiments, the devices of the present invention can be used to measure the influence of biomaterials on a biomechanical response. For example, differential contraction of vascular smooth muscle remodeling due to variation in material properties (e.g., stiffness, surface topography, surface chemistry or geometric patterning) of polymeric thin films can be studied.

In further embodiments, the devices of the present invention can be used to study functional differentiation of stem cells (e.g., pluripotent stem cells, multipotent stem cells, induced pluripotent stem cells, and progenitor cells of embryonic, fetal, neonatal, juvenile and adult origin) into contractile phenotypes. For example, undifferentiated cells, e.g., stem cells, are coated on the thin films and differentiation into a contractile phenotype is observed by thin film bending. Differentiation into an anisotropic tissue may also be observed by quantifying the degree of alignment of sarcomeres and/or quantifying the orientational order parameter (OOP). Differentiation can be observed as a function of: co-culture (e.g., co-culture with differentiated cells), paracrine signaling, pharmacology, electrical stimulation, magnetic stimulation, thermal fluctuation, transfection with specific genes, chemical and/or biomechanical perturbation (e.g., cyclic and/or static strains).

In one embodiment a biomechanical perturbation is stretching of, e.g., the flexible polymer layer during tissue formation. In one embodiment, the stretching is cyclic stretching. In another embodiment, the stretching is sustained stretching.

In one embodiment, the flexible polymer layer is stretched at an appropriate time after cell seeding that is based on the type(s) of cells seeded. In one embodiment, the flexible polymer layer is stretched at about minutes, hours, or days after cell seeding onto a patterned flexible polymer layer. In one embodiment, the flexible polymer layer is stretched at about 0, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, or about 3.0 hours after cell seeding onto a patterned flexible polymer layer.

In one embodiment, the flexible polymer layer is patterned isotropically. Stretching, therefore, results in the formation of anisotropic tissue, the anisotropy of which is in the direction of the stretch.

In another embodiment, the flexible polymer layer is patterned anistropically and stretching enhances the anisotropy of the tissue formed.

In one embodiment, the flexible polymer layer is stretched using about a 0.1, 0.2, 0.3, 0.4, 0.5, 1.0, 1.5, 2.0, 2.5, 3.0, 3.5, 4, 4.5, 5.0, 5.5, 6.0, 6.5, 7.0, 7.5, 8.0, 8.5, 9.0, 9.5, or about 10.0 Hertz (Hz) cyclic stretch. In one embodiment, the flexible polymer layer is stretched using about 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, or about 20.0% strength sustained stretch.

In another embodiment, the devices of the invention may be used to determine the toxicity of a test compound by evaluating, e.g., the effect of the compound on an electrophysiological response of an MTF. For example, opening of calcium channels results in influx of calcium ions into the cell, which plays an important role in excitation-contraction coupling in cardiac and skeletal muscle fibers. The reversal potential for calcium is positive, so calcium current is almost always inward, resulting in an action potential plateau in many excitable cells. These channels are the target of therapeutic intervention, e.g., calcium channel blocker subtype of anti-hypertensive drugs. Candidate drugs may be tested in the electrophysiological characterization assays described herein to identify those compounds that may potentially cause adverse clinical effects, e.g., unacceptable changes in cardiac excitation, that may lead to arrhythmia.

For example, unacceptable changes in cardiac excitation that may lead to arrhythmia include, e.g., blockage of ion channel requisite for normal action potential conduction, e.g., a drug that blocks $Na^+$ channel would block the action potential and no upstroke would be visible; a drug that blocks $Ca^{2+}$ channels would prolong repolarization and increase the refractory period; blockage of $K^+$ channels would block rapid repolarization, and, thus, would be dominated by slower $Ca^{2+}$ channel mediated repolarization.

In addition, metabolic changes may be assessed to determine whether a test compound is toxic by determining, e.g., whether contacting with a test compound results in a decrease in metabolic activity and/or cell death. For example, detection of metabolic changes may be measured using a variety of detectable label systems such as fluormetric/chrmogenic detection or detection of bioluminescence using, e.g., AlamarBlue fluorescent/chromogenic determination of REDOX activity (Invitrogen), REDOX indicator changes from oxidized (non-fluorescent, blue) state to reduced state (fluorescent, red) in metabolically active cells; Vybrant MTT chromogenic determination of metabolic activity (Invitrogen), water soluble MTT reduced to insoluble formazan in metabolically active cells; and Cyquant NF fluorescent measurement of cellular DNA content (Invitrogen), fluorescent DNA dye enters cell with assistance from permeation agent and binds nuclear chromatin. For bioluminescent assays, the following exemplary reagents is used: Cell-Titer Glo luciferase-based ATP measurement (Promega), a thermally stable firefly luciferase glows in the presence of soluble ATP released from metabolically active cells.

The devices of the invention are also useful for evaluating the effects of particular delivery vehicles for therapeutic agents e.g., to compare the effects of the same agent administered via different delivery systems, or simply to assess whether a delivery vehicle itself (e.g., a viral vector or a liposome) is capable of affecting the biological activity of the MTF. These delivery vehicles may be of any form, from conventional pharmaceutical formulations, to gene delivery vehicles. For example, the devices of the invention may be used to compare the therapeutic effect of the same agent administered by two or more different delivery systems (e.g., a depot formulation and a controlled release formulation). The devices and methods of the invention may also be used to investigate whether a particular vehicle may have effects of itself on the tissue. As the use of gene-based therapeutics increases, the safety issues associated with the various possible delivery systems become increasingly important. Thus, the devices of the present invention may be used to investigate the properties of delivery systems for nucleic acid therapeutics, such as naked DNA or RNA, viral vectors (e.g., retroviral or adenoviral vectors), liposomes and the like. Thus, the test compound may be a delivery vehicle of any appropriate type with or without any associated therapeutic agent.

Furthermore, the devices of the present invention are a suitable in vitro model for evaluation of test compounds for therapeutic activity with respect to, e.g., a muscular and/or neuromuscular disease or disorder. For example, the devices of the present invention (e.g., comprising muscle cells) may be contacted with a candidate compound by, e.g., diffusion of the test compound added drop-wise on the surface of an MTF, diffusion of a test compound through the culture medium, or immersion in a bath of media containing the test compound, and the effect of the test compound on muscle activity (e.g., a biomechanical and/or electrophysiological activity) may measured as described herein, as compared to an appropriate control, e.g., an untreated MTF. Alternatively, a device of the invention may be bathed in a medium containing a candidate compound, and then the cells are washed, prior to measuring a muscle activity (e.g., a biomechanical and/or electrophysiological activity) as described herein. Any alteration to an activity determined using the device in the presence of the test agent (as compared to the same activity using the device in the absence of the test compound) is an indication that the test compound may be useful for treating or preventing a muscle disease, e.g., a neuromuscular disease.

For use in the methods of the invention, the cells seeded onto the MTF may be normal muscle cells (cardiac, smooth, or skeletal muscle cells), abnormal muscle cells (e.g., those derived from a diseased tissue, or those that are physically or genetically altered to achieve a abnormal or pathological phenotype or function), normal or diseased muscle cells derived from embryonic stem cells or induced pluripotent stem cells, or normal cells that are seeded/printed onto the film in an abnormal or aberrant configuration. In some cases, both muscle cells and neuronal cells are present on the film.

Evaluation of muscle activity includes determining the degree of contraction, i.e., the degree of curvature or bend of the muscular film, and the rate or frequency of contraction/rate of relaxation compared to a normal control or control film in the absence of the test compound. An increase in the degree of contraction or rate of contraction indicates that the compound is useful in treatment or amelioration of pathologies associated with myopathies such as muscle weakness or muscular wasting. Such a profile also indicates that the test compound is useful as a vasocontractor. A decrease in the degree of contraction or rate of contraction is an indication that the compound is useful as a vasodilator and as a therapeutic agent for muscle or neuromuscular disorders characterized by excessive contraction or muscle thickening that impairs contractile function.

Compounds evaluated in this manner are useful in treatment or amelioration of the symptoms of muscular and neuromuscular pathologies such as those described below. Muscular Dystrophies include Duchenne Muscular Dystrophy (DMD) (also known as Pseudohypertrophic), Becker Muscular Dystrophy (BMD), Emery-Dreifuss Muscular Dystrophy (EDMD), Limb-Girdle Muscular Dystrophy (LGMD), Facioscapulohumeral Muscular Dystrophy (FSH or FSHD) (Also known as Landouzy-Dejerine), Myotonic Dystrophy (MMD) (Also known as Steinert's Disease), Oculopharyngeal Muscular Dystrophy (OPMD), Distal Muscular Dystrophy (DD), and Congenital Muscular Dystrophy (CMD). Motor Neuron Diseases include Amyotrophic Lateral Sclerosis (ALS) (Also known as Lou Gehrig's Disease), Infantile Progressive Spinal Muscular Atrophy (SMA, SMA1 or WH) (also known as SMA Type 1, Werdnig-Hoffman), Intermediate Spinal Muscular Atrophy (SMA or SMA2) (also known as SMA Type 2), Juvenile Spinal Muscular Atrophy (SMA, SMA3 or KW) (also known as SMA Type 3, Kugelberg-Welander), Spinal Bulbar Muscular Atrophy (SBMA) (also known as Kennedy's Disease and X-Linked SBMA), Adult Spinal Muscular Atrophy (SMA). Inflammatory Myopathies include Dermatomyositis (PM/DM), Polymyositis (PM/DM), Inclusion Body Myositis (IBM). Neuromuscular junction pathologies include Myasthenia Gravis (MG), Lambert-Eaton Syndrome (LES), and Congenital Myasthenic Syndrome (CMS). Myopathies due to endocrine abnormalities include Hyperthyroid Myopathy (HYPTM), and Hypothyroid Myopathy (HYPOTM). Diseases of peripheral nerves include Charcot-Marie-Tooth Disease (CMT) (Also known as Hereditary Motor and Sensory Neuropathy (HMSN) or Peroneal Muscular Atrophy (PMA)), Dejerine-Sottas Disease (DS) (Also known as CMT Type 3 or Progressive Hypertrophic Interstitial Neuropathy), and Friedreich's Ataxia (FA). Other Myopathies include Myotonia Congenita (MC) (Two forms: Thomsen's and Becker's Disease), Paramyotonia Congenita (PC), Central Core Disease (CCD), Nemaline Myopathy (NM), Myotubular Myopathy (MTM or MM), Periodic Paralysis (PP) (Two forms: Hypokalemic-HYPOP- and Hyperkalemic-HYPP) as well as myopathies associated with HIV/AIDS.

The methods and devices of the present invention are also useful for identifying therapeutic agents suitable for treating or ameliorating the symptoms of metabolic muscle disorders such as Phosphorylase Deficiency (MPD or PYGM) (Also known as McArdle's Disease), Acid Maltase Deficiency (AMD) (Also known as Pompe's Disease), Phosphofructokinase Deficiency (PFKM) (Also known as Tarui's Disease), Debrancher Enzyme Deficiency (DBD) (Also known as Cori's or Forbes' Disease), Mitochondrial Myopathy (MITO), Carnitine Deficiency (CD), Carnitine Palmityl Transferase Deficiency (CPT), Phosphoglycerate Kinase Deficiency (PGK), Phosphoglycerate Mutase Deficiency (PGAM or PGAMM), Lactate Dehydrogenase Deficiency (LDHA), and Myoadenylate Deaminase Deficiency (MAD).

In addition to the disorders listed above, the screening methods described herein are useful for identifying agents suitable for reducing vasospasms, heart arrhythmias, and cardiomyopathies.

Vasodilators identified as described above are used to reduce hypertension and compromised muscular function associated with atherosclerotic plaques. Smooth muscle cells associated with atherosclerotic plaques are characterized by an altered cell shape and aberrant contractile function. Such cells are used to populate a thin film, exposed to candidate compounds as described above, and muscular function evaluated as described above. Those agents that improve cell shape and function are useful for treating or reducing the symptoms of such disorders.

Smooth muscle cells and/or striated muscle cells line a number of lumen structures in the body, such as uterine tissues, airways, gastrointestinal tissues (e.g., esophagus, intestines) and urinary tissues, e.g., bladder. The function of smooth muscle cells on thin films in the presence and absence of a candidate compound may be evaluated as described above to identify agents that increase or decrease the degree or rate of muscle contraction to treat or reduce the symptoms associated with a pathological degree or rate of contraction. For example, such agents are used to treat gastrointestinal motility disorders, e.g., irritable bowel syndrome, esophageal spasms, achalasia, Hirschsprung's disease, or chronic intestinal pseudo-obstruction.

The present invention is next described by means of the following examples. However, the use of these and other examples anywhere in the specification is illustrative only, and in no way limits the scope and meaning of the invention or of any exemplified form. The invention is not limited to any particular preferred embodiments described herein. Many modifications and variations of the invention may be apparent to those skilled in the art and can be made without departing from its spirit and scope. The contents of all references, patents and published patent applications cited throughout this application, including the figures, are incorporated herein by reference.

EXAMPLES

Example 1: Muscular Thin Film Device and Use Thereof for Determining a Contractile Function A. Substrate Fabrication Polydimethylsiloxane (PDMS) thin film substrates were fabricated via a multi-step spin coating process. Poly(N-isopropylacrylamide) (PIPAAm) (Polysciences, Inc.) was dissolved at 10 wt % in 99.4% 1-butanol (w/v) and spun coat onto the glass cover slips. Sylgard 184 (Dow Corning) polydimethylsiloxane (PDMS) elastomer was mixed at a 10:1 base to curing agent ratio, doped with 0.1% by volume 0.2 μm Fluorospheres (Invitrogen), and spin coated on top of the PIPAAm coated glass cover slip. Polydimethylsiloxane-coated cover slips were then cured.

B. ECM Patterning

The polydimethylsiloxane thin films were coated with either an isotropic or anisotropic layer of extracellular matrix (ECM) (e.g. fibronectin, laminin, collagen I). In each case, immediately prior to ECM treatment, the polydimethylsiloxane-coated cover slips were UV ozone treated for 8 minutes to sterilize the surface and increase hydrophilicity. All subsequent processing was performed in a biohood under sterile conditions.

ECM patterning was performed using microcontact printing (μCP). The basic μCP technique is well established and allows the rapid patterning of biomolecules on a variety of planar substrates using polydimethylsiloxane stamps. The variation employed here used a polydimethylsiloxane stamp to pattern ECM proteins on the polydimethylsiloxane coated glass cover slips to form anisotropic 2D myocardium. ECM proteins were transferred from the stamp to the polydimethylsiloxane thin film by making conformal contact for 1 minute.

C. 1. Vascular Smooth Muscle Seeding and Culture

Human umbilical artery vascular smooth muscle was seeded on thin films at 300 cells/mm$^2$ in complete M199 medium (M199 supplemented with 10% fetal bovine serum (FBS), penicillin, streptomycin, L-glutamine, glucose and vitamin B12). The tissue was cultured in complete M199 for 48 hours, with a single media change at 24 hours. After 48 hours, the cells were serum starved for an additional 48 hours (M199 supplemented with penicillin, streptomycin, L-glutamine, glucose and vitamin B12, but no FBS).

2. Neonatal Rat Ventricular Myocytes Seeding and Culture

Neonatal rat ventricular myocytes were isolated from 2-day old neonatal Sprague-Dawley rats based on published methods. Briefly, ventricles were extracted and homogenized by washing in Hanks balanced salt solution followed by digestion with trypsin and collagenase with agitation overnight at 4° C. Cells were re-suspended in M199 culture medium supplemented with 10% (v/v) heat-inactivated fetal bovine serum (FBS), 10 mM HEPES, 3.5 g/L glucose, 2 mM L-glutamine, 2 mg/L vitamin B-12, and 50 U/ml penicillin and seeded on anisotropically patterned FN at a density of 1 million cells per cover slip. Samples were incubated under standard conditions at 37° C. and 5% CO2. Media was exchanged with maintenance media (2% FBS) every 48 h until use. The MTFs were cultured for a period of 4-6 days and then used in the contractility assay.

D. Thin Film Release

Polydimethylsiloxane films were transferred to a petri dish of Tyrode's solution at 37° C. The Petri dish was placed on a stereomicroscope with darkfield illumination and cut into rectangles, parallel with tissue orientation, using a razor blade. Once the Tyrode's solution cools below 35° C., the PIPAAm layer transitions from a hydrophobic state to a hydrophilic state and begins to dissolve. Once the PIPAAm dissolves, films are pulled free of the coverslip with tweezers.

E. Experimental Testing Parameters (Tyrodes, Pacing, Video Recording)

Muscle thin films were transferred to fresh Tyrode's solution in the testing dish (FIG. 1), which is maintained at 37° C. by a peltier heating system. Films were adhered to Teflon coated posts (FIG. 3) by moving them into close contact using tweezers. The films were imaged using a stereomicroscope outfitted with fluorescent imaging capability. Both brightfield and fluorescent images were captured every thirty seconds. In the experiment shown in FIG. 4, four films were treated with 50 nM endothelin-1 followed by 100 µM HA-1077 (fasudil).

F. Image and Stress Analysis

Quantification and analysis of thin film motion was performed using ImageJ (NIH) and MATLAB software. Thresholded fluorescent images (FIG. 4 B) were fit to circles whose radii of curvature could be measured (FIG. 4C). Using elasticity theory, the contraction stress necessary to induce the measured changes in curvature were calculated (FIG. 4D).

Results

Muscular thin films were engineered using both cardiomyocytes (cMTFs) and vascular smooth muscle cells (vMTFs). MTFs were constructed by seeding dissociated muscle cells on a multilayer polymer substrate. PIPAAm was spin coated onto a glass coverslip and PDMS is spin coated onto of the PIPAAm layer. The cells were seeded on ECM proteins micropatterned onto the PDMS layer. When the media temperature was lowered below 35° C., the PIPAAm dissolves and the MTF was released and free floating. The radius of curvature of the resulting bilaminate structure is indicative of the stress in the cell layer.

In order to guide alignment of the cells, lines of ECM proteins (FN or LAM) were microcontact printed onto the PDMS. Atomic Force Microscopy (AFM) surface scanning revealed that this ECM pattern is approximately 10-20 nm in thickness. When cells were cultured on the patterned ECM, they spontaneously organize into a contiguous tissue that is aligned with the patterned matrix lines.

In these cells, the long axis of the cell and the nuclear eccentricity parallel the underlying matrix pattern. Fluorescent staining of the fixed tissues revealed that the actin aligns with the underlying matrix in the vascular smooth muscle. In cardiac muscle the sarcomeric Z-lines are perpendicular to the matrix. In both cases, the cytoskeletal architecture indicates that the primary axis of contraction is in the longitudinal direction.

Cardiac ventricular MTFs (cMTFs) were used to measure systolic contraction stress and contractile wave speed in engineered myocardial tissues. The cMTFs were engineered as anisotropic, with uniaxial cellular alignment. Imaging of the Z-disks by immunostaining sarcomeric α-actinin confirmed that alignment of the myofibrils was also anisotropic. The cMTFs were mounted in a bath with a PDMS clamp to firmly hold the cMTF in place during rapid movement and parallel platinum wire electrodes to field stimulate muscle contraction. During diastole, the cMTF may have a baseline curvature due to resting tension in the tissue construct. During contraction, the radius of curvature decreases dramatically, due to cardiomyocytegenerated stress of 13.9 kPa. In this set of experiments, three cMTFs built from the ventricular myocytes harvested from two different rat pup litters produced a mean peak systolic stress of 9.2±3.5 kPa.

The cMTF goes through substantial bending and deformation during contraction, however, because the cMTF is a thin beam, the actual shortening of the cardiomyocytes is <1%, i.e. contraction is isometric. Knowing the stress generated by the cMTF and the elastic modulus of the cardiomyocytes (E=~30 kPa), the unconstrained shortening was estimated as 25% at peak systole. The accurate measurement of the cell and PDMS layer thicknesses are critical for calculating the contraction stress and unconstrained shortening. The elastic modulus of the cell layer, however, has little affect on the calculated stress but does have a significant effect is on the calculation of λa, so calculating unconstrained shortening is strongly dependent on accurate cell modulus measurements.

The cMTF system is able to provide an estimate of the contractile wave velocity based on the mechanical deformation of the cMTFs. Tracking the mechanicalwave requires that contraction in the cMTF initiates at one end and propagates to the other. Spontaneous contraction of cMTFs often initiated at the free end and propagated to the base. Tracking the initial position and propagation of maximum curvature along the cMTF from the initiation of contraction until peak systole (uniform curvature) enabled estimation of contractile wave propagation. In the example shown here, the contractilewave speed was 1.875 cm/s, comparable to the velocity of the mechanical wave reported using phase imaging techniques.

Vascular MTFs (vMTFs) were used to demonstrate the potential of this method as a pharmaceutical screening assay. Human umbilical artery VSMCs were engineered as anisotropic monolayers aligned parallel to the long axis of the MTF. The vMTFs were adhered to PTFE coated posts via hydrophobic interaction with the PDMS. This arrangement allowed multiple vMTFs to be viewed concurrently. Here, eight vMTFs were tested using this assay. The fluorosphere doped PDMS could be viewed using fluorescent stereomicroscopy. In this arrangement, the films are easily approximated as circular arcs.

The vMTFs were treated with the endothelium-produced vasoconstrictor endothelin-1 followed by the rho-kinase inhibitor HA-1077, in order to calculate all of the relevant stress states of arterial muscle. The vMTFs had an initial stable baseline curvature indicating that the cells generated a basal stress, defined as the sum of the passive residual stress and the basal contractile tone, of 17.1±1.7 kPa. This value represents the resting tension of the tissue. At time 0, the vMTFs were stimulated with 50 nM ET-1, inducing contraction, which caused a decrease in their radii of curvature as the cell generated stress increased by 5.06±0.75 kPa. Treatment with 100 mM HA-1077, a rho-kinase inhibitor, caused a rapid increase in radius of curvature, due to inhibition of contraction (FIG. 6G), and resulted in a stress of 3.1±0.8 kPa. The HA-1077 dosage is sufficient to inhibit all myosin light chain phosphorylation, so this value represents the residual stress, or the stress generated by the cytoskeletal elements not involved in the contractile apparatus, but which remains after all other loads are removed. By comparing the residual stress following HA-1077 treatment to the pre ET-1 treated tissue, it can be can determined that the vMTFs had a basal contractile tone of 13.1±2.1 kPa. This protocol demonstrates that the vMTFs are able to mimic well documented native vascular behavior and implies that this assay could be used to test the effects of pharmaceutical agents on vascular contractility.

The measured peak systolic stress and constrained shortening of the muscle thin films (MTF) fabricated using neonatal rat ventricular myocytes as described above, were comparable to isometric measurement of isolated papillary muscle. Thus, this MTF system recapitulates both the anisotropic alignment of normal cardiac muscle and physiologically relevant, systolic stress levels.

A unique aspect of the MTF contractility assay is the capability to track local changes in radius of curvature along its length during the cardiac cycle. Further, dyssynchronous contraction when the mechanical wave fails to propagate, or initiates at multiple locations at the same time, resulting in a fluttering cMTF with no discernable deflection can be detected. Thus, a broad range of qualitative and quantitative data can be extracted from the assay by proper frame by frame analysis of the deformation.

The vascular smooth muscle cell MTFs were used to mimic the lamellae of the arterial tunica media. The vMTF assay confirms the presence of functional ET-1 receptors in the engineered smooth muscle and is able to accurately quantify the magnitude of induced contraction. Concurrent monitoring of eight vMTFs contracting and relaxing demonstrates that this technique produces engineered smooth muscle that repeatability responds to pharmacologic stimulation at physiologic stress levels. Moreover, this assay demonstrates that MTFs can provide a method for studying diseases and potential therapeutic interventions, with the potential to significantly scale up the throughput. As an early screening method, this high-fidelity, in vitro contractility assay could be used to directly test the effect of drugs on contractility and potentially decrease the high failure rate of cardiovascular drugs, as currently, novel molecules reaching Phase 1 clinical trials for cardiovascular drugs have a completion rate of less than 20%.

The methods and devices described above and below for the preparation of mucle thin films (MTFs) permit the preparation of a more relevant in vitro model of engineered tissue in that the engineered tissue displays one or more properties of mature tissues, e.g., mature electrophysiology, such as mature action potential morphology, mature ion channel expression, and mature contractility, rather than the immature properties displayed by tissues/cells cultured using previously described methods. Also see, e.g., WO 2008/051265.

Example 2: Cardiac Myocytes and Muscular Thin Film High Content, Enhanced Throughput Device and Use Thereof for Determining a Contractile Function A. Substrate Fabrication Polydimethylsiloxane (PDMS) thin film substrates were fabricated via a multi-step spin coating process. Poly(N-isopropylacrylamide) (PIPAAm) (Polysciences, Inc.) was dissolved at 10 wt % in 99.4% 1-butanol (w/v) and the PIPAAm is deposited in the mid-section of the cover-slip (as shown in FIG. 7A(i)). Sylgard 184 (Dow Corning) polydimethylsiloxane (PDMS) elastomer was mixed at a 10:1 base to curing agent ratio and spun coat on top of the PIPAAm coated glass cover slip (FIG. 7A(ii)). Polydimethylsiloxane-coated cover slips were then cured.

Substrates suitable for the horizontal muscle thin films were also fabricated using Sylgard 184 (Dow Corning) polydimethylsiloxane (PDMS) elastomer mixed at a 10:1 base to curing agent ratio, doped with 0.1% by volume 0.2 µm Fluorospheres (Invitrogen), and spun coated on top of the PIPAAm coated glass cover slip which were then cured.

B. Fibronectin Anisotropic Patterning

The PDMS thin films were coated with an anisotropic layer of fibronectin (FN). In each case, immediately prior to fibronectin treatment, the PDMS-coated cover slips were UV ozone treated for 8 minutes to sterilize the surface and increase hydrophilicity. All subsequent processing was performed in a biohood under sterile conditions.

Anisotropic patterning of fibronectin was performed using microcontact printing (µCP). The basic µCP technique is well established and allows the rapid patterning of biomolecules on a variety of planar substrates using PDMS stamps. The variation employed here used a polydimethylsiloxane stamp to pattern fibronectin on the polydimethylsiloxane coated glass cover slips to form anisotropic 2D myocardium. Fibronectin (50 µg/mL fibronectin in sterile deionized (DI) water) was transferred from the stamp to the polydimethylsiloxane thin film by making conformal contact for 1 minute. The stamp was position in such a way that the pattern is perpendicular to the PIPAAm deposit (FIG. 7A(iv)). The films were then incubated for 15 minutes in low concentration fibronectin (2.550 µg/mL fibronectin in sterile DI water). Following incubation, excess fibronectin was removed by washing 3 times with a sterile phosphate buffer solution (PBS) and then left in PBS until seeding.

C. Cardiomyocyte Seeding and Culture

Neonatal rat ventricular myocytes were isolated from 2-day old neonatal Sprague-Dawley rats based on well known methods. Cells were diluted to a concentration of ~350,000 per mL in seeding media (SM) (M199 media supplemented with 10% FBS), and 3 mL was seeded on each cover slip. After 24 hours incubation, the cover slips were washed 3 times with phosphate buffered saline (PBS) to remove non-adherent cells and recovered with SM. After an additional 24 hours, the media was exchanged with maintenance media (MM) [M199 media supplemented with 2% fetal bovine serum (FBS)] to minimize growth of fibroblasts inevitably present in the primary harvest cardiomyocyte population.

D. Releasing the Films for a Contractility Study

MTFs were released from the cover slip once the cells have formed the appropriate 2D microstructure. The MTFs were either cut out by hand, cut out using a robotic system, pre-cut prior to cell incubation. In one specific example of, e.g., horizontal MTF production, the middle section was cut out, so that only eight rectangles remained in the area that had PIPAAm (see FIG. 7A(vi) for example of the cutout shape). Once the Tyrode's solution cools below 35° C., the PIPAAm layer transitions from a hydrophobic state to a hydrophilic state and begins to dissolve. As the PIPAAm dissolved the middle section cutout was peeled off the substrate with a pair of tweezers. Once the PIPAAm dissolves completely, the contraction of the myocytes pulls the MTF (the remaining rectangles) free from the rigid substrate. In the case of the horizontal MTF, rectangles remain with one end partially fixed to the substrate (FIG. 7A(vii)).

E. Experimental Testing Parameters (Tyrodes, Pacing, Video Recording)

Actuation and observation of multiple MTFs was carried out in a physiologic solution (e.g., normal Tyrodes solution). MTFs were electrically paced using parallel platinum wire electrodes spaced ~1 cm apart and lowered directly into the center of the Petri dish. An external field stimulator (Myopacer, IonOptix) was used to apply a 10-20 V, 10 msec duration square wave between the electrodes at pacing rates from 0.5 to 2 Hz.

F. Video and Image Analysis

Figure 7D:
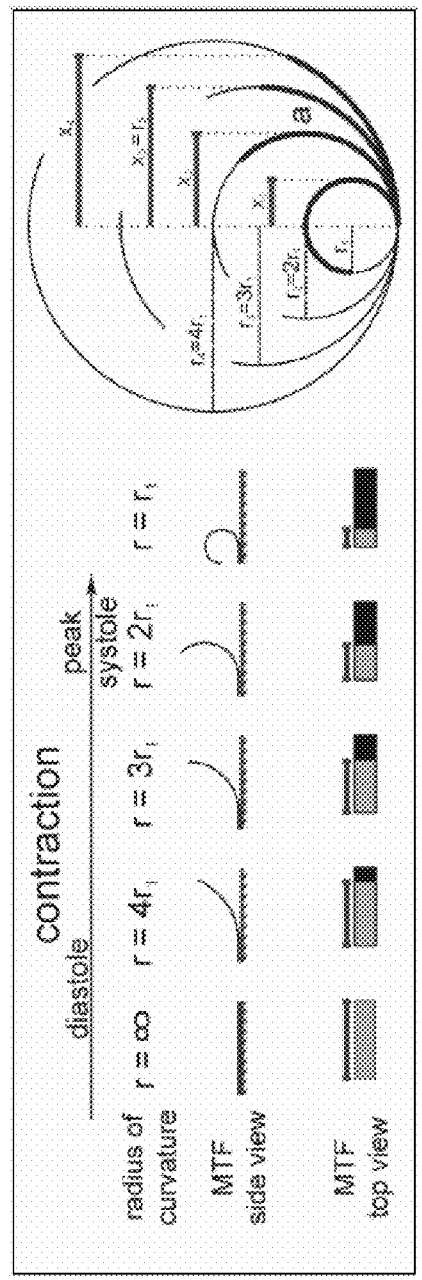

Quantification and analysis of thin film motion was performed using ImageJ (NIH) (FIG. 7B) and MATLAB software. From the thresholded fluorescent images the films length was tracked throughout the contraction and the radius of curvature calculated (FIGS. 7C and 7D). Using elasticity theory, the contraction stress necessary to induce the measured changes in curvature were calculated.

Example 3: Multi-Well Plate Tissue Contractility Device and Assay

This example describes the fabrication of a multi-well plate with micropatterned bottom surfaces wherein each well is used in a horizontal muscular thin film (MTF) assay (see, e.g., FIG. 9A). The micropatterned multi-well plates are especially amenable to assays using automatic imaging of the MTFs in, e.g., a GE InCellAnalyzer.

The multi-well plate with MTF assay, can be used for biomechanical measurements of myocyte contraction properties. In this device the tissue constructs remain partially fixed to a hard substrate, such as the glass bottom of the multi-well plate. This invention is designed for use with polymeric thin films (PCT Publication No. WO 2008/051265 A2), but could be used with any differentially stressed polymer or tissue construct. In this assay the thin films bend up from the viewing (horizontal) plane unlike the original thin film assay in which a single film bends in the viewing plane. The number of wells is limited by the size of the desired films (the films have to be large enough for the cells to constitute a tissue), with a film of at least 1.2 mm×2.4 mm any 6, 12, 24, 48, 96 well plates can be used. The assay may be utilized to measure biomechanical forces due to a number of stimuli including, but not limited to, contraction, osmotic swelling, structural remodeling and tissue level pre-stress. It is possible to further automate the assay by methods that include, but are not limited to, cookie cutter razors that would come down into the wells to cut the films, programmable lasers that cut the films, and automatic aspiration pipettes to aspirate out unwanted film sections. The biomechanical responses due to paracrine signaling events can also be studied through the addition of a co-culture system, making the device attractive for studying cell-to-cell drug effects.

In the context of the present experiment a section of glass was cut to match the dimensions of the multi-well plate skeleton section of glass (7.5 cm×11 cm) and was covered with a protective film (to preserve the optical clarity of the substrate during later fabrication steps), by lowering the protective film onto the glass covered with 200 proof ethyl alcohol, and removing, e.g., using pressure, the excess ethanol from under the film. This process was repeated for the other side of the glass and then islands corresponding to a portion of the wells were cut out of the top protective film. Then, a temperature sensitive polymer, specifically poly(N-isopropylacrylamide) (PIPAAm), was deposited in a thin layer onto the open glass islands and the top protective film layer was peeled off. A biopolymer, specifically polydimethylsiloxane (PDMS), was deposited in a layer, e.g., by spin coating, (~5-25 µm) on top of the whole glass, with the bottom protective film preventing back-splatter of the PDMS onto the glass. The PDMS was allowed to completely cure overnight and the bottom protective film was peeled off.

A biopolymer, e.g., extracellular matrix protein (ECM), e.g., fibronectin (FN), was stamped (micro-contact printed) in a pattern onto the PDMS.

In parallel, a second section of glass was cut to match the dimensions of the multi-well plate skeleton (7.5 cm×11 cm). The second glass section was then spin coated with a layer of PDMS, which was immediately brought into contact with and lifted off of the bottom of the multi-well plate skeleton leaving behind a thin layer of PDMS on the bottom of the multi-well plate skeleton. At this point, the ECM patterned PDMS-glass base was pressed into contact with the PDMS coated bottom of the multi-well plate skeleton (24 well A-Plate GBMP Black Porvair Sciences Ltd.), creating a PDMS seal between the wells. To provide additional liquid load bearing capacity, a sealant was painted around the outer border, further adhering the glass base to the multi-well plate skeleton. The plate was then placed in a humid warm (37° C.) incubator overnight to complete the PDMS seal curing while providing the humidity necessary to maintain proper ECM molecule activity.

Phenol red was placed inside various wells of the plate to confirm that the seal between wells did not leak. Following a 48-hour incubation, the phenol red had not spread to adjacent wells demonstrating that the seals of the wells were intact (see, e.g., FIG. 9B).

Contractile cells, specifically cardiomyocytes, were seeded onto the ECM inside each well. For the multi-well plate, the MTFs inside the film with the cells were cut and the unwanted regions peeled off the glass in each well. As a result a single rectangle of film remained attached to the glass at one edge only in each well. The dynamics of these tissue constructs was recorded. The cells in the plate can be fixed and immuno-stained to study cell structure (see, e.g., FIG. 9C).

Example 4: High-Throughput Multi-Tissue Contractility Device and Assay

A multi-tissue contractility assay can be used, for example, to qualitatively compare contractions of two tissue types, to compare the effect of one tissue response in proximity to another tissue, or for biomechanical measurements of myocyte contraction properties.

The substrates for use in a multi-tissue contractility assay are made as described below and herein. In this device, the tissue constructs remain partially fixed to a rigid substrate, e.g., the glass bottom of the multi-well plate, and bend up from the viewing (horizontal) plane. The rigid substrate is made in such a manner that it can be split after the ECM has been patterned into as many parts, at least two, as the number of tissues. Different types of cells are then cultured on the substrate or different types of micropatterning can be patterned onto the substrate, e.g., line patterns, anisotropic monolayers, or isotropic monolayers. The assay could be utilized to measure biomechanical forces due to a number of stimuli including, but not limited to contraction, osmotic swelling, structural remodeling and tissue level pre-stress. The biomechanical responses due to paracrine signaling events can also be studied, making the device attractive for studying cell-to-cell drug effects.

One benefit of the methods described below is the ability to maintain even thickness of the sacrificial polymer layer from island to island, thus, yielding more consistent devices.

In the context of the present experiment and as depicted in FIGS. 10 and 11, a section of glass (7.5 cm×11 cm) was covered with a protective film, by lowering the protective film onto the glass covered with 200 proof ethyl alcohol, and removing, e.g., using pressure, the excess ethanol from under the film. This process was repeated for the other side of the glass and then islands corresponding to the desired size of assay were cut out of the top film. A temperature sensitive polymer, specifically poly(N-isopropylacrylamide) (PIPAAm), was then deposited as a thin layer onto the open glass islands, then the top protective film layer was peeled off. A polymer, specifically polydimethylsiloxane (PDMS), was deposited in a layer (~5-25 µm) on top of the whole glass, with the bottom protective film preventing backsplatter of the PDMS onto the glass. The PDMS was allowed to completely cure overnight and the bottom protective film was peeled off. A mask, printed on transparencies was used to cut the glass into desired shapes. An extracellular matrix protein, such as (ECM) fibronectin (FN), was stamped in the pattern depicted in FIGS. 10 and 11 onto the PDMS. The glass was cut in between the two PIPAAm islands. The two pieces of glass were treated with different agents (Pluronic F127 blocking and low concentration FN background). Contractile cells, such as cardiomyocytes, were seeded onto the ECM. The cells formed lines in the first (Pluronics treated) tissue, and anisotropic monolayers in the second tissue (low concentration FN treated). The cover-slips were then combined and the films cut, with the unwanted regions peeled away. As a result a single rectangle of film remained attached to the glass at one edge only. The dynamics of these tissue constructs were recorded.

Example 5: Vascular Smooth Muscle Thin Film High Content, Enhanced Throughput Device and Use Thereof for Determining a Contractile Function A. Substrate Fabrication A section of glass (7.5 cm×11 cm) was covered with a static vinyl protective film by lowering the protective film onto the glass, and removing, e.g., using pressure, the all air bubble from under the film. This process was repeated for the other side of the glass and then islands corresponding to the desired size of assay were cut out of the top film.

Polydimethylsiloxane (PDMS) thin film substrates were fabricated via a multi-step spin coating process. Poly(N-isopropylacrylamide) (PIPAAm) (Polysciences, Inc.) was dissolved at 10 wt % in 99.4% 1-butanol (w/v) and was then deposited as a thin layer onto the open glass islands, then the top protective film layer was peeled off. Sylgard 184 (Dow Corning) polydimethylsiloxane (PDMS) elastomer was mixed at a 10:1 base to curing agent ratio doped with 0.1% by volume 0.2 mm Fluorospheres (Invitrogen), and spun coated on top of the PIPAAm coated glass cover slip which was then cured. The next day, the bottom protective film was peeled off. A mask, printed on transparencies was used to cut the glass into desired shapes.

B. Fibronectin Anisotropic Patterning

The PDMS thin films were coated with an anisotropic layer of fibronectin (FN). In each case, immediately prior to fibronectin treatment, the PDMS-coated cover slips were UV ozone treated for 8 minutes to sterilize the surface and increase hydrophilicity. All subsequent processing was performed in a biohood under sterile conditions.

Anisotropic patterning of fibronectin was performed using microcontact printing (mCP). The basic mCP technique is well established and allows the rapid patterning of biomolecules on a variety of planar substrates using PDMS stamps. The variation employed here used a polydimethylsiloxane stamp to pattern fibronectin on the polydimethylsiloxane coated glass cover slips to form anisotropic 2D myocardium. Fibronectin (50 µg/mL fibronectin in sterile deionized (DI) water) was transferred from the stamp to the polydimethylsiloxane thin film by making conformal contact for 1 minute. The stamp was positioned in such a way that the pattern is perpendicular to the PIPAAm deposit. Following stamping, excess fibronectin was removed by washing 3 times with a sterile phosphate buffer solution (PBS) and then left dry until seeding.

C. Neonatal Rat Ventricular Myocytes Seeding and Culture

Neonatal rat ventricular myocytes were isolated from 2-day old neonatal Sprague-Dawley rats based on published methods. Briefly, ventricles were extracted and homogenized by washing in Hanks balanced salt solution followed by digestion with trypsin and collagenase with agitation overnight at 4° C. Cells were re-suspended in M199 culture medium supplemented with 10% (v/v) heat-inactivated fetal bovine serum (FBS), 10 mM HEPES, 3.5 g/L glucose, 2 mM L-glutamine, 2 mg/L vitamin B-12, and 50 U/ml penicillin and seeded on anisotropically patterned FN at a density of 1 million cells per cover slip. Samples were incubated under standard conditions at 37° C. and 5% CO2. Media was exchanged with maintenance media (2% FBS) every 48 h until use. The MTFs were cultured for a period of 4-6 days and then used in the contractility assay.

D. Releasing the Films for a Contractility Study

MTFs were released from the cover slip once the cells have formed the appropriate 2D microstructure. The MTFs were either cut out by hand, cut out using a robotic system, pre-cut prior to cell incubation. In one specific example of, e.g., horizontal MTF production, the middle section was cut out, so that only six rectangles remained in the area that had PIPAAm). Once the Tyrode's solution cools below 35° C., the PIPAAm layer transitions from a hydrophobic state to a hydrophilic state and begins to dissolve. As the PIPAAm dissolved the middle section cutout was peeled off the substrate with a pair of tweezers. Once the PIPAAm dissolves completely, the contraction of the myocytes pulls the MTF (the remaining rectangles) free from the rigid substrate. In the case of the horizontal MTF, rectangles remain with one end partially fixed to the substrate.

E. Experimental Testing Parameters (Tyrodes, Pacing, Video Recording)

Actuation and observation of multiple MTFs was carried out in a physiologic solution (e.g., normal Tyrodes solution). The horizontal MTFs (hMTFs) fabricated with vascular smooth muscle cells in the presence of fluorescent beads were treated with the endothelium-produced vasoconstrictor endothelin-1 (ET-1) followed by the rho-kinase inhibitor HA-1077.

Figure 12:
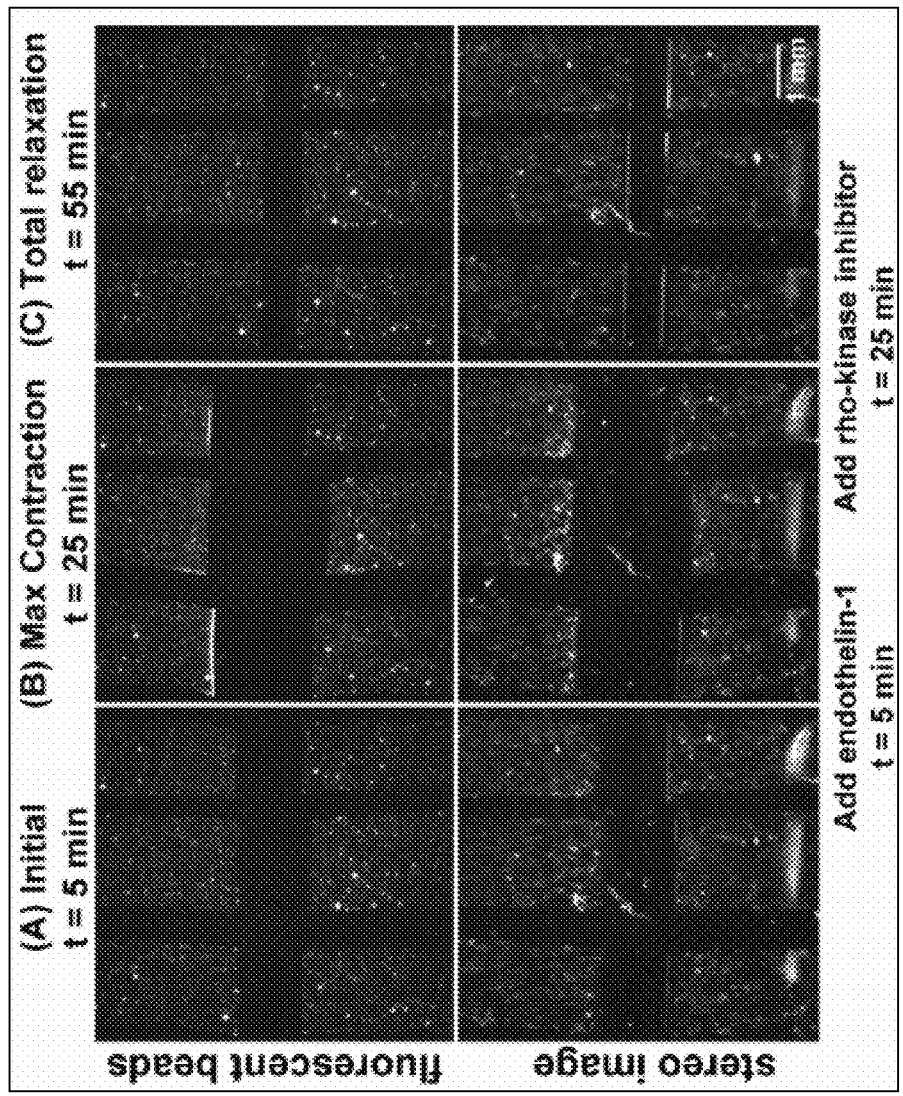
FIG. 12 contrasts the use of fluorescent microscopy and the use of brightfield stereo microscopy of vascular smooth muscle (VSM) horizontal MTFs during an assay of the invention as described in Example 5. The top row depicts fluorescent microscopy photographs of VSM horizontal MTFs comprising fluorescent beads embedded in the PDMS film. The bottom row shows brightfield stereo microscopy images of the same films. (A) Photographs taken 5 minutes after the start of the experiment, the films are slightly bent up from the glass due to the initial contraction of VSM. (B) Photographs taken 20 minutes after addition of the vasoconstrictor (Endothilin-1), which causes the VSM to contract and the films to bend up from the glass. (C) Photographs taken 30 minutes after addition of a rho-kinase inhibitor, which causes the VSM to completely relax and the films to lie flat on the glass. The contrast of the use of fluorescent microscopy shows that fluorescent images may be used to eliminate noise that may be present in regular brightfield images.
Figure 13A:
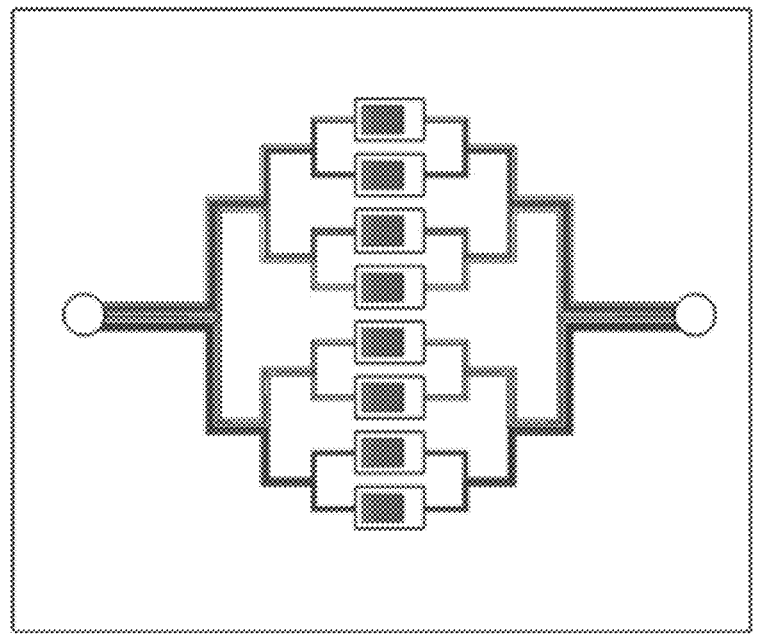
FIG. 13A is a top view schematic representation of one embodiment of the devices of the invention depicting MTFs enclosed in individual chambers of a microfluidics device. Utilizing microfluidic principles of laminar flow and mixing, a small amount of nanoparticles or small molecules can be diluted into a wide variety of concentrations in simultaneous assays for tissue function.
Figure 13B:
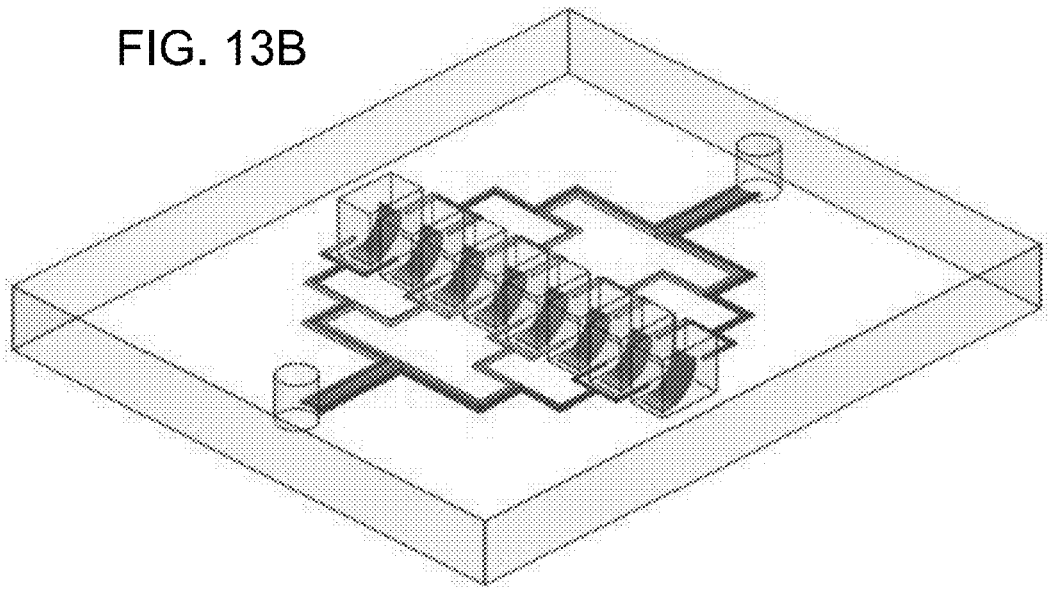
FIG. 13B is a side view schematic representation of one embodiment of the devices of the invention depicting MTFs enclosed in individual chambers of a microfluidics device. Utilizing microfluidic principles of laminar flow and mixing, a small amount of nanoparticles or small molecules can be diluted into a wide variety of concentrations in simultaneous assays for tissue function.
Figure 14:
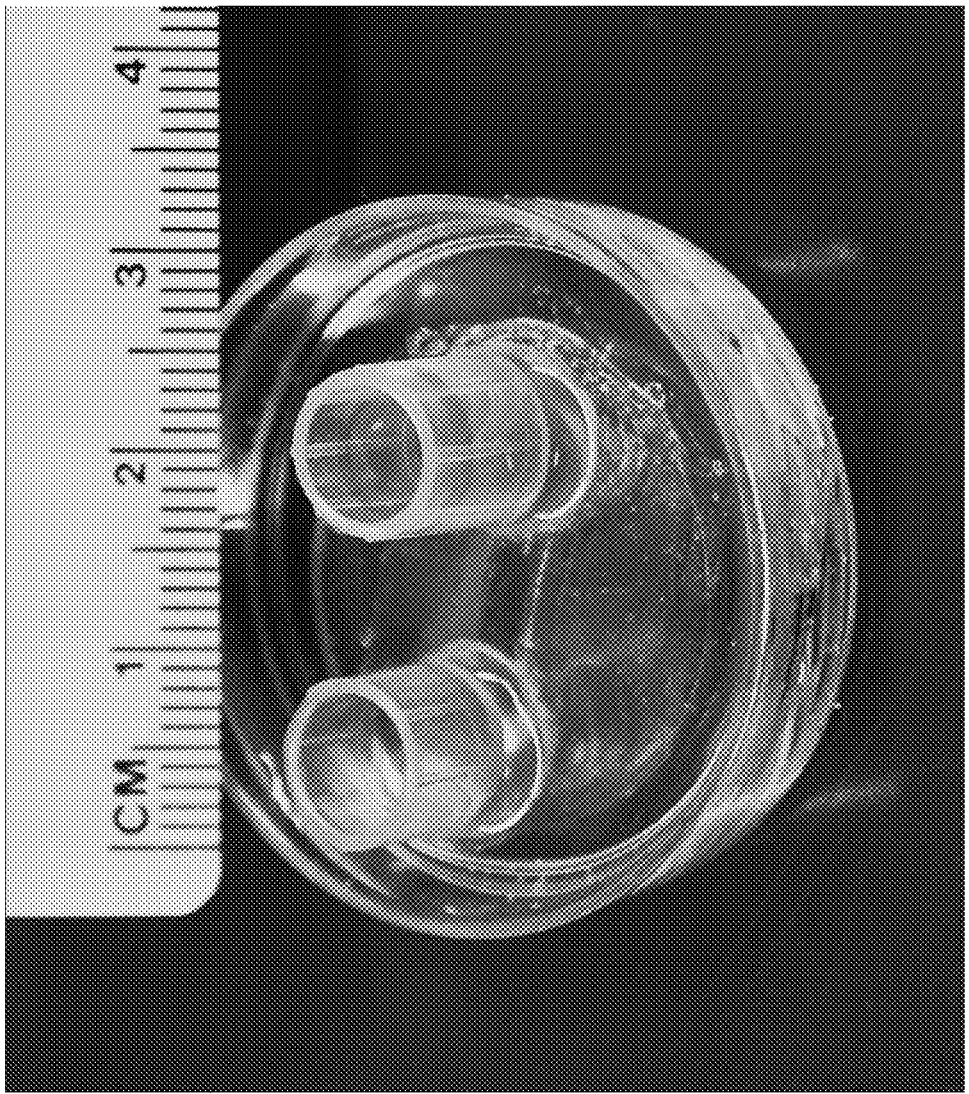
FIG. 14 is a photograph of one embodiment of the devices of the invention depicting a tri-laminate fluidic chamber comprising an MTF and useful in the methods of the invention, such as, a contractility assay. The device is constructed from 1.5 mm PMMA. Number 1 glass cover slips comprise the top and bottom layers. Muscular Thin Films (MTFs) were cut into approximately 1 mm×3 mm cantilevers before assembling the device.
Figure 15:
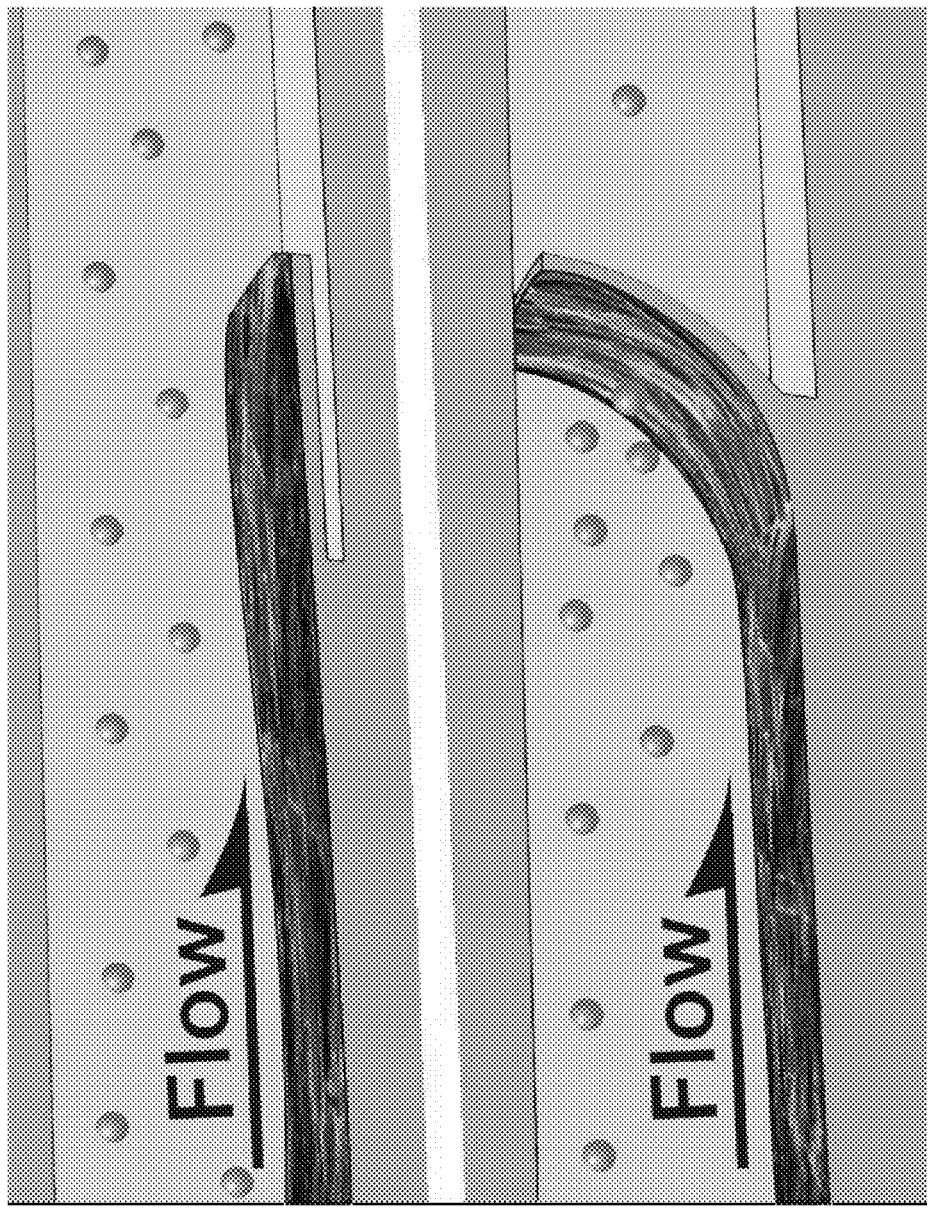
FIG. 15 depicts an anisotropic MTF in a microfluidic chamber exposed to a drug (circles) in diastole (top) and at peak systole (bottom).
Figure 16:
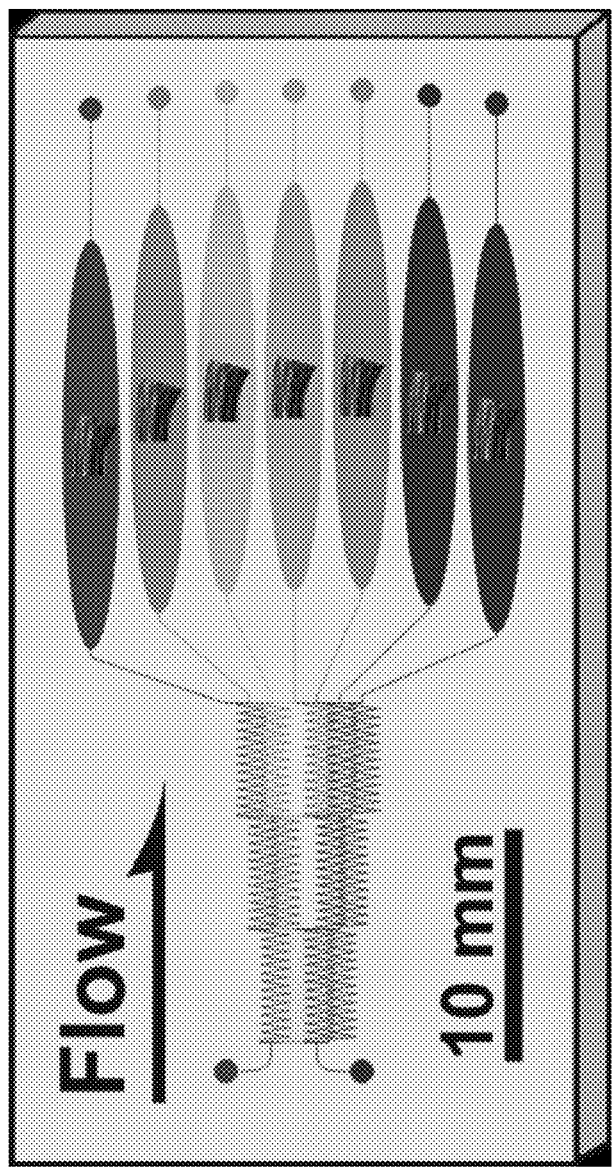
FIG. 16 is a schematic representation of a gradient generation microfluidic device to assay drug-dose responses. The PDMS-based device (25 mm×75 mm), receives three fluids at left, the highest drug dose in the top channel, a decreased drug concentration in the middle channel, and isotonic buffer in the bottom channel. The microfluidic devices generate drug gradients which are then separated and transferred into wide (2.5 mm) channels to decrease fluid velocity in order to simplify fluid dynamics calculations for horizontal MTF (hMTF) assays.
Figure 17:
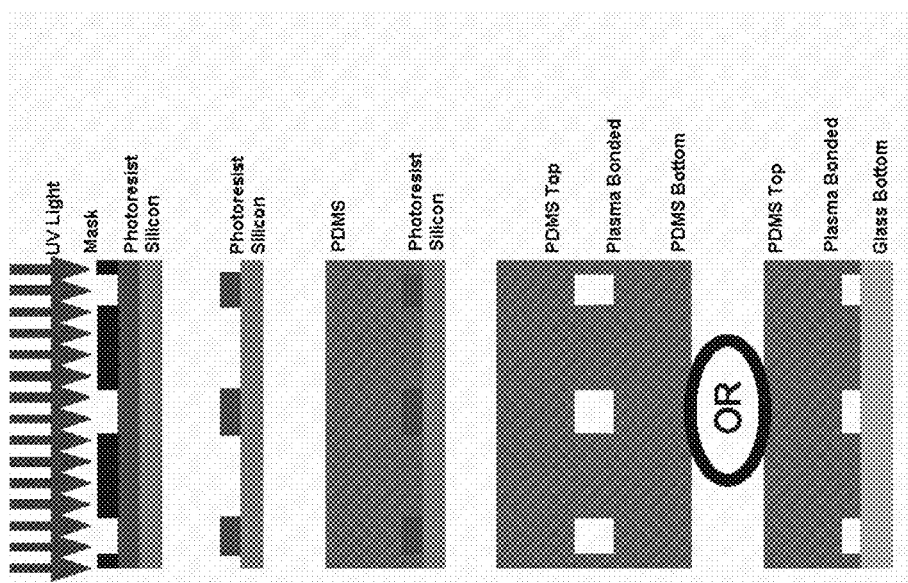
FIG. 17 is a schematic representation illustrating soft lithography-based microfluidic fabrication of one embodiment of the devices of the invention. A negative photoresist underneath a mask is exposed to UV light crosslinking the exposed photoresist. The un-crosslinked photoresist is developed, leaving a negative mold. PDMS elastomer is poured into the photoresist/silicon mold and peeled away after curing. The patterned PDMS can be either bonded to another PDMS pattern or planar polymeric surface via plasma-treated surface covalent bonding.
Figure 18:
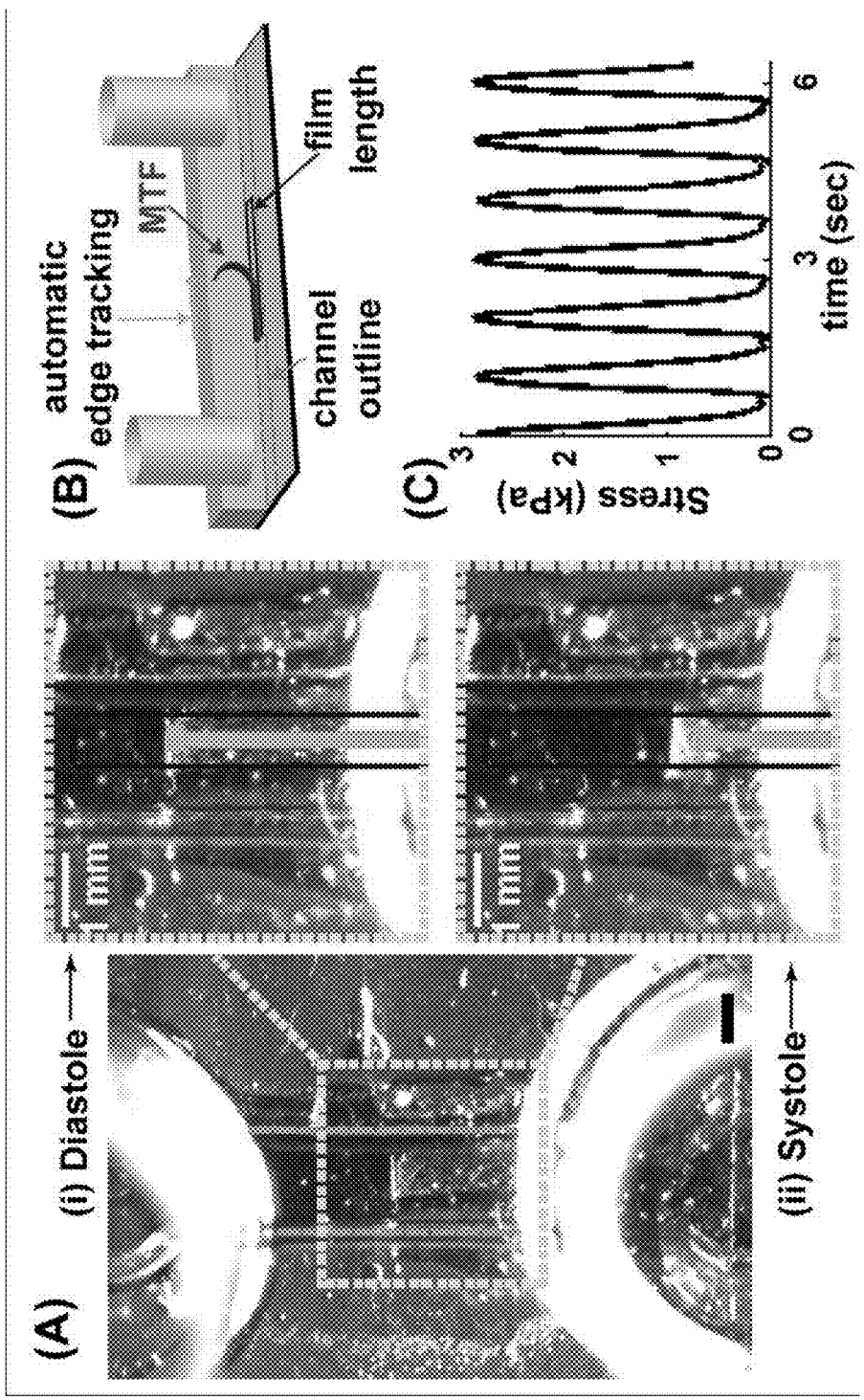
FIG. 18 is a photograph of the top view of a microfluidic channel with a hMTF inside the channel. The inflow, outflow channel are outlined with a dashed light gray line. The myocytes are paced inside the channel and the diastolic and peak systolic positions of the hMTF are shown inside the boxes, with the film edge tracked (light gray) and the film length outlined (black). (B) Schematic showing the microfluidic channel with a hMTF inside, MTF film in medium gray, initial length outline in black, edge tracking in light gray, channel outline in light gray. (C) Filtered stress profile read-out from this film in kPa.

The hMTFs had an initial stable baseline curvature (FIG. 12) indicating that the cells generated a basal stress. At time 0, the hMTFs were stimulated with 50 nM ET-1, inducing contraction, which caused a decrease in their radii of curvature (FIG. 12). Treatment with 100 mM HA-1077, a rho-kinase inhibitor, caused a rapid increase in radius of curvature, due to inhibition of contraction.

This protocol demonstrates that the hMTFs are able to mimic well documented native vascular behavior and implies that this assay could be used to test the effects of pharmaceutical agents on vascular contractility.

F. Video and Image Analysis

Quantification and analysis of thin film motion was performed using ImageJ (NIH) and MATLAB software. From the thresholded fluorescent images the length of the projection of the film on the horizontal plane was tracked throughout the contraction and the radius of curvature calculated.

Using elasticity theory, the contraction stress necessary to induce the measured changes in curvature were calculated.

EQUIVALENTS

In describing embodiments of the invention, specific terminology is used for the sake of clarity. For purposes of description, each specific term is intended to at least include all technical and functional equivalents that operate in a similar manner to accomplish a similar purpose. Additionally, in some instances where a particular embodiment of the invention includes a plurality of system elements or method steps, those elements or steps may be replaced with a single element or step; likewise, a single element or step may be replaced with a plurality of elements or steps that serve the same purpose. Further, where parameters for various properties are specified herein for embodiments of the invention, those parameters can be adjusted up or down by 1/20th, 1/10th, 1/5th, 1/3rd, 1/2, etc., or by rounded-off approximations thereof, unless otherwise specified. Moreover, while this invention has been shown and described with references to particular embodiments thereof, those skilled in the art will understand that various substitutions and alterations in form and details may be made therein without departing from the scope of the invention; further still, other aspects, functions and advantages are also within the scope of the invention. The contents of all references, including patents and patent applications, cited throughout this application are hereby incorporated by reference in their entirety. The appropriate components and methods of those references may be selected for the invention and embodiments thereof. Still further, the components and methods identified in the Background section are integral to this disclosure and can be used in conjunction with or substituted for components and methods described elsewhere in the disclosure within the scope of the invention.

What is claimed:

1. A device for measuring a contractile function, the device comprising:
   a plurality of horizontal muscle thin films,
   wherein each of said plurality of horizontal muscle thin films is fabricated on a rigid planar base layer, wherein each includes a portion released from the underlying rigid planar base on which it was fabricated, and each remains attached at one end to the underlying rigid planar base layer on which it was fabricated for use in the device,
   wherein a portion of the rigid planar base layer underneath the portion of each of said plurality of horizontal muscle thin films released from the underlying rigid planar base on which it was fabricated is transparent and a remaining portion of the rigid planar base layer is opaque,
   wherein said plurality of muscle thin films each comprise an opaque flexible polymer layer and a population of isolated muscle cells seeded on the flexible polymer layer in a predetermined pattern, and wherein said predetermined pattern allows for the alignment of the cells such that a functional tissue which can perform a contractile function is formed.

2. A device for measuring a contractile function, the device comprising:
   a plurality of horizontal muscle thin films,
   wherein each of said plurality of horizontal muscle thin films is fabricated on a rigid planar base layer, wherein each includes a portion released from the underlying rigid planar base on which it was fabricated, and each remains attached at one end to the underlying rigid planar base layer on which it was fabricated for use in the device,
   wherein a portion of the rigid planar base layer underneath the portion of each of said plurality of horizontal muscle thin films released from the underlying rigid planar base on which it was fabricated is transparent and a remaining portion of the rigid planar base layer is opaque; and
   a photodiode array,
   wherein the plurality of muscle thin films each comprise an opaque flexible polymer layer and a population of isolated muscle cells seeded on the flexible polymer layer in a predetermined pattern, and wherein said predetermined pattern allows for the alignment of the cells such that a functional tissue structure which can perform a contractile function is formed.

3. The method of claim 1 or 2, further comprising a second base layer seeded with a second population of cells.

4. The device of claim 1 or 2, wherein the base layer is a glass coverslip, a Petri dish, strips of glass, glass slides, or a multi-well plate.

5. The device of claim 1 or 2, wherein the muscle cells are cardiomyocytes.

6. The device of claim 1 or 2, further comprising a solid support structure, said solid support structure comprising a plurality of cell culture wells or a multi-well plate skeleton; an optical signal capture device; and an image processing software to calculate change in an optical signal.

7. The device of claim 1 or 2, further comprising a solid support structure, said solid support structure comprising one or more microfluidics chambers, or two or more inlet microchannels and one or more outlet microchannels.

8. The device of claim 1 or 2, wherein said plurality of muscle thin films comprise vascular smooth muscle cells or vascular endothelial cells.

9. The device of claim 1 or 2, wherein said plurality of muscle thin films comprise smooth muscle cells or striated muscle cells.

10. A method for identifying a compound that modulates a contractile function, the method comprising
    providing the device of claim 1 or 2;
    contacting the plurality of said horizontal muscle thin films with a test compound; and
    determining the effect of the test compound on a contractile function in the presence and absence of the test compound, wherein a modulation of the contractile function in the presence of said test compound as compared to the contractile function in the absence of said test compound indicates that said test compound modulates a contractile function, thereby identifying a compound that modulates a contractile function.

11. The method of claim 10, wherein the contractile function is a biomechanical activity.

12. The method of claim 10, wherein the contractile function is an electrophysiological activity.

13. The method of claim 10, wherein the plurality of muscle thin films are cultured in the presence of a fluorophor.

14. The method of claim 10, wherein said plurality of muscle thin films comprises cardiomyocytes.

15. The method of claim 10, wherein said plurality of muscle thin films comprises vascular smooth muscle cells or vascular endothelial cells.

16. The method of claim 10, wherein said plurality of muscle thin films comprises smooth muscle cells or striated muscle cells.

17. A method for identifying a compound useful for treating or preventing a muscle disease, the method comprising
  providing the device of claim 1 or 2;
  contacting the plurality of said horizontal muscle thin films with a test compound; and
  determining the effect of the test compound on a contractile function in the presence and absence of the test compound, wherein a modulation of the contractile function in the presence of said test compound as compared to the contractile function in the absence of said test compound indicates that said test compound modulates a contractile function, thereby identifying a compound useful for treating or preventing a muscle disease.

18. The method of claim 17, wherein the contractile function is a biomechanical activity.

19. The method of claim 17, wherein the contractile function is an electrophysiological activity.

20. The method of claim 17, wherein the plurality of muscle thin films are cultured in the presence of a fluorophor.

21. The method of claim 17, wherein said plurality of muscle thin films comprises cardiomyocytes.

22. The method of claim 17, wherein said plurality of muscle thin films comprises vascular smooth muscle cells or vascular endothelial cells.

23. The method of claim 17, wherein said plurality of muscle thin films comprises smooth muscle cells or striated muscle cells.

* * * * *

UNITED STATES PATENT AND TRADEMARK OFFICE
CERTIFICATE OF CORRECTION

| | | |
|---|---|---|
| PATENT NO. | : 9,719,982 B2 | Page 1 of 1 |
| APPLICATION NO. | : 14/642906 | |
| DATED | : August 1, 2017 | |
| INVENTOR(S) | : Kevin Kit Parker et al. | |

It is certified that error appears in the above-identified patent and that said Letters Patent is hereby corrected as shown below:

In the Specification

At Column 1, Line number 21, delete ", in whole or in part,".

Signed and Sealed this
Fourteenth Day of October, 2025

John A. Squires
*Director of the United States Patent and Trademark Office*